(12) United States Patent
Weinshilboum et al.

(10) Patent No.: US 7,858,306 B2
(45) Date of Patent: Dec. 28, 2010

(54) HSD3B1 SEQUENCE VARIANTS

(75) Inventors: Richard M. Weinshilboum, Rochester, MN (US); Linda L. Pelleymounter, Rochester, MN (US); Eric D. Wieben, Rochester, MN (US); Oreste Salavaggione, St. Louis, MO (US); Liewei Wang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 631 days.

(21) Appl. No.: 11/482,514

(22) Filed: Jul. 7, 2006

(65) Prior Publication Data

US 2009/0023136 A1    Jan. 22, 2009

Related U.S. Application Data

(60) Provisional application No. 60/697,212, filed on Jul. 7, 2005.

(51) Int. Cl.
C12Q 1/68 (2006.01)
C07H 21/00 (2006.01)
C07H 21/02 (2006.01)
C07H 21/04 (2006.01)

(52) U.S. Cl. .................. 435/6; 536/22.1; 536/23.1; 536/24.3

(58) Field of Classification Search ............ 435/6; 536/22.1, 23.1, 24.3
See application file for complete search history.

(56) References Cited

U.S. PATENT DOCUMENTS

| | | | |
|---|---|---|---|
| 5,451,683 A | 9/1995 | Barrett et al. | |
| 5,733,729 A | 3/1998 | Lipshutz et al. | |
| 5,770,722 A | 6/1998 | Lockhart et al. | |
| 5,869,296 A * | 2/1999 | Nag et al. | 435/91.3 |
| 2001/0053519 A1 * | 12/2001 | Fodor et al. | 435/6 |
| 2002/0192643 A1 * | 12/2002 | Reed | 435/6 |

FOREIGN PATENT DOCUMENTS

| | | |
|---|---|---|
| WO | WO 98/20019 | 5/1998 |
| WO | WO 99/57318 | 11/1999 |
| WO | WO0179552 | * 10/2001 |

OTHER PUBLICATIONS

Chang et al., Joint effect of HSD3B1 and HSD3B2 genes is associated with hereditary and sporadic prostate cancer susceptibility. Cancer Research. 62(6): 1784-1789 (2002).*

Rosmond et al., Polymorphism in exon 4 of the human 3.beta.-hydroxysteroid dehydrogenase type I gene (HSD3B1) and blood pressure. Biochemical and Biophysical Research Communications. 293 (1) : 629-632 (2002).*

Varma et al. Molecular cloning and functional characterisation of a glucose transporter, CaHGT1, of *Candida albicans*. FEMS microbiology letters. 182 (1): 15-21 (Jan. 1, 2000).*

Lachance et al., Characterization of human 3.beta.-hydroxysteroid dehydrogenase/.DELTA.5-.DELTA.4-isomerase gene and its expression in mammalian cells. Journal of Biological Chemistry 265 (33) : 20469-75 (1990).*

Saiki et al.Genetic analysis of amplified DNA with immobilized sequence-specific oligonucleotide probes PNAS 86(16) : 6230-4 (1989).*

GenBank Accession No. NM_000862 dated Nov. 18, 2006, 4 pages.

GenBank Accession No. NT_004754 dated Feb. 19, 2004, 2 pages.

Caine et al., "Recombinant Human Phenylethanolamine N-Methyltransferase: Overproduction in *Escherichia coli*, Purification, and Characterization," *Protein Expr. Purif.*, 1996, 8(2):160-166.

Carbunaru et al., "The Hormonal Phenotype of Nonclassic 3 β-Hydroxysteroid Dehydrogenase (HSD3B) Deficiency in Hyperandrogenic Females Is Associated with Insulin-Resistant Polycystic Ovary Syndrome and Is Not a Variant of Inherited HSD3B2 Deficiency," *J. Clin. Endocrinol. Metab.*, 2004, 89(2):783-794.

Chadwick et al., "Heterozygote and Mutation Detection by Direct Automated Fluorescent DNA Sequencing Using a Mutant Taq DNA Polymerase," *BioTechniques*, 1996, 20(4):676-683.

Chang et al., "Joint Effect of *HSD3B1* and *HSD3B2* Genes Is Associated with Hereditary and Sporadic Prostate Cancer Susceptibility," *Cancer Res.*, 2002, 62:1784-1789.

Cibelli et al., "Cloned Transgenic Calves Produced from Nonquiescent Fetal Fibroblasts," *Science*, 1998, 280:1256-1258.

Cleland, "Computer programmes for processing enzyme kinetic data," *Nature*, 1963, 198:463-465.

Cole et al., "The EBV-Hybridoma Technique and Its Application to Human Lung Cancer," *Monoclonal Antibodies and Cancer Therapy*, 1985, Alan R. Liss, Inc., pp. 77-96.

Cote et al., "Generation of human monoclonal antibodies reactive with cellular antigens," *Proc. Natl. Acad. Sci. USA*, 1983, 80:2026-2030.

Excoffier and Slatkin, "Maximum-Likelihood Estimation of Molecular Haplotype Frequencies in a Diploid Population," *Mol. Biol. Evol.*, 1995, 12(5):921-927.

Gordon et al., "*Consed*: A Graphical Tool for Sequence Finishing," *Genome Res.*, 1998, 8:195-202.

Guatelli et al., "Isothermal, in vitro amplification of nucleic acids by a multienzyme reaction modeled after retroviral replication," *Proc. Natl. Acad. Sci. USA*, 1990, 87:1874-1878.

Hacia et al., "Detection of heterozygous mutations in *BRCA1* using high density oligonucleotide arrays and two-colour fluorescence analysis," *Nature Genet.*, 1996, 14:441-447.

Hartl and Clark, "Chromosomes and Heredity," *Principles of Population Genetics*, 1997, 3rd edition, Sinauer Associates, Inc., (Sunderland, MA), pp. 96-106.

(Continued)

Primary Examiner—Ethan Whisenant
(74) *Attorney, Agent, or Firm*—Fish & Richardson P.C.

(57) ABSTRACT

Isolated HSD3B1 nucleic acid molecules that include a nucleotide sequence variant and nucleotides flanking the sequence variant are described, as are HSD3B1 allozymes. Methods for determining whether a subject contains an HSD3B1 sequence variant also are provided.

6 Claims, 11 Drawing Sheets

OTHER PUBLICATIONS

Hedrick, "An Introduction to Gametic Disequilibrium," *Genetics of Populations*, 2000, 2nd edition, Jones and Bartlett (Sudbury, MA), pp. 396-406.

Huse et al., "Generation of a Large Combinatorial Library of the Immunoglobulin Repertoire in Phage Lambda," *Science*, 1989, 246:1275-1281.

Hyrup and Nielsen, "Peptide Nucleic Acids (PNA): Synthesis, Properties and Potential Applications," *Bioorgan. Med. Chem.*, 1996, 4(1):5-23.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lewis, "PCR's Competitors Are Alive and Well and Moving Rapidly Towards Commercialization," *Genetic Engineering News*, 1992, 12(9):1-3.

Long et al., "An E-M Algorithm and Testing Strategy for Multiple-Locus Haplotypes," *Am. J. Hum. Genet.*, 1995, 56:799-810.

McBride et al., "The human 3β-hydroxysteroid dehydrogenase (3β-HSD) gene cluster on chromosome 1p13 contains a presumptive pseudogene; 3β-HSD and CYP17 do not segregate with dominantly inherited hirsutism," *J. Mol. Endocrinol.*, 1995, 15(2):167-176.

Morel et al., "Structure-function relationships of 3β-hydroxysteroid dehydrogenase: Contribution made by the molecular genetics of 3β-hydroxysteroid dehydrogenase deficiency," *Steroids*, 1997, 62:176-184.

Morissette et al., "Genetic linkage mapping of HSD3B1 and HSD3B2 encoding human types I and II 3β-hydroxysteroid dehydrogenase/$\Delta^5$-$\Delta^4$-isomerase close to D1S514 and the centromeric D1Z5 locus," *Cytogenet. Cell Genet.*, 1995, 69:59-62.

Myakishev et al., "High-Throughout SNP Genotyping by Allele-Specific PCR with Universal Energy-Transfer-Labeled Primers," *Genome Research*, 2001, 11:163-169.

Nickerson et al., "PolyPhred: automating the detection and genotyping of single nucleotide substitutions using fluorescence-based resequencing," *Nucl. Acids Res.*, 1997, 25(14):2745-2751.

Peng et al., "Transcription Enhancer Factor-5 and a GATA-Like Protein Determine Placental-Specific Expression of the Type I Human 3β-Hydroxysteroid Dehydrogenase Gene, HSD3B1," *Mol. Endocrinol.*, 2004, 18(8):2049-2060.

Prince et al., "Robust and Accurate Single Nucleotide Polymorphism Genotyping by Dynamic Allele-Specific Hybridization (DASH): Design Criteria and Assay Validation," *Genome Res.*, 2001, 11:152-162.

Rosmond et al., "Polymorphism in exon 4 of the human 3β-hydroxysteroid dehydrogenase type I gene (HSD3B1) and blood pressure," *Biochem. Biophys. Res. Commun.*, 2002, 293:629-632.

Sambrook et al., *Molecular Cloning, A Laboratory Manual*, 1989, Section 9.34-9.55, second edition, Cold Spring Harbor Press, Plainview, NY.

Schafer and Hawkins, "DNA variation and the future of human genetics," *Nat. Biotechnol.*, 1998, 15:33-39.

Shastry, "Gene disruption in mice: Models of development and disease," *Mol. Cell. Biochem.*, 1998, 181:163-179.

Ausubel et al., "Immunology," *Short Protocols in Molecular Biology*, 1992, Chapters 8 and 11, Green Publishing Associates and John Wiley & Sons.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug Dev.*, 1997, 7(3):187-195.

Terwilliger and Ott, "Linkage Disequilibrium between Alleles at Marker Loci," *Handbook of Human Genetic Linkage*, 1994, The Johns Hopkins University Press, Baltimore, pp. 188-193.

Thomas et al., "Structure/Function Relationships Responsible for Coenzyme Specificity and the Isomerase Activity of Human Type 1 3β-Hydroxysterood Dehydrogenase/Isomerase," *J. Biol. Chem.*, 2003, 278(37):35483-35490.

Thomas et al., "Structure/Function Relationships Responsible for the Kinetic Differences between Human Type 1 and Type 2 3β-Hydroxysteroid Dehydrogenase and for the Catalysis of the Type 1 Activity," *J. Biol. Chem.*, 2002, 277(45):42795-42801.

Underhill et al., "Detection of Numerous Y Chromosome Biallelic Polymorphisms by Denaturing High-Performance Liquid Chromatography," *Genome Res.*, 1997, 7:996-1005.

Wakayama et al., "Full-term development of mice from enucleated oocytes injected with cumulus cell nuclei," *Nature*, 1998, 394:369-374.

Weiss, "Hot Prospect for New Gene Amplifier," *Science*, 1991, 254:1292-1293.

Wilkinson, "Statistical Estimations in Enzyme Kinetics," *Biochem. J.*, 1961, 80:324-332.

Wilmut et al., "Viable offspring derived from fetal and adult mammalian cells," *Nature*, 1997, 385:810-813.

Wong et al., "Human GM-CSF: Molecular Cloning of the Complementary DNA and Purification of the Natural and Recombinant Proteins," *Science*, 1985, 228:810-815.

* cited by examiner

Figure 1 – page 1

| | | |
|---|---|---|
| 1 | TTGCCTATGA GGTAGATTGG GGGAAGGTCA GGGAATTAAC AGGGAACAGG CAGAAAACAA | 60 |
| 61 | CTTTCTGGAG TGACGGAAAT GGTCTATATC TTTTTTGGGG TGCTACTTAC ATGGGCATAT | 120 |
| 121 | ATAACTGTCA AGTTCCACTG AACTGAACAC TGAAGACCTG GCATTTTAA TGCATGTAAA | 180 |
| 181 | TTATATTTCA ATTTTTTTGA GTAAAGTGTC TTGGGAAGCT TATGGCGGTG ATATTTGGGC | 240 |
| 241 | AGTTCTGGGG CATAGGCTTC AGAAGCATTC ACAGTATGTC CAGTTCAAGA ATTTGCTGAG | 300 |
| 301 | AATCGTTTTG CAGCCAAAAA TATGGATAAG TTCGAACACC TATGATAAGA GTCATTGGGG | 360 |
| 361 | CATACAACCA CAAATCCCCA CTCTTGTGAT ACAGGCCATA TCATTAAGTG GTTATCACCA | 420 |
| 421 | GATAGCTTTC CTTCAATGAT GTTGTTCATC TAGGAACCCA GGGCTCTCCA GGGGCAAATG | 480 |
| 481 | ACCATTGAGG TTTCAGATAT ATTGGGTAGG AAAGAAAGTC ACCTCACATA AAACTAAGTG | 540 |
| 541 | ATTGGAGCTG TCACCATTGC AAATTTCTAA ATTTTGTAAG ACAGCAGCAA CATTTCAAAT | 600 |
| 601 | GATAGTCTGA GAGAGGAGAT AATGGGCTTA CATGGATTTC CCTCCAGATG GATTTACTGA | 660 |
| 661 | ACAAGGGCAC AATTCAAATT GCACTTGCAG ATTTCTCCTG GTCTAGTTTA AGTTCACAGA | 720 |
| 721 | TTGTGGATCC CAGACAGCTG GTATCAACTG ACTAGTGTCC TGTTAAGGCT AAACCCAAGA | 780 |
| 781 | CTCTTTGCCA CACTGCAGCA TTAGGATGGG ACTTCTCTTC CTGTTCCTGG AAGAATTAG | 840 |
| 841 | AGATGTAACC CAAAGGTCAC TATTTTTCTG AGATAAGGAT CCCATAGGAG GAGAGAGCAA | 900 |
| 901 | TGAGTACATG GCCAGAGATC AAAGTGATAA GGGTTGGGCC AGAAGCCACA GTGCATAAAG | 960 |
| 961 | CTTCAGACTT GCCACAGGAA ATGAGGTGAG AAGTACGTCC ACTCTTCTGT CCAGCTTTTA | 1020 |
| 1021 | ACAATCTAAC TAATGGTTAG AGATTTTTCA TTTTCTTTCA GCTACTCCTG CAGTGGTGGG | 1080 |
| 1081 | GACACAGAAT GTTTGCAAAA AAAATGGGGT GGAGGAAAAT GAGGCATCTG TGTGAGTATA | 1140 |
| 1141 | TAACCATTTG ACATCTCTTT TTAGCCCTCT CCAGGGTCAC CCTAGAATCA GATCTGCTCC | 1200 |
| 1201 | CCAGCATCTT CTGTTTCCTG GTGAGTGATT CCTGCTACTT TGGATGGCCA TGACGGGCTG | 1260 |
| |                                                                                            M  T  G  W | |
| 1261 | GAGCTGCCTT GTGACAGGAG CAGGAGGGTT TCTGGGACAG AGGATCATCC GCCTCTTGGT | 1320 |
| |  S  C  L    V  T  G    A  G  G  F    L  G  Q    R  I  I    R  L  L  V | |
| 1321 | GAAGGAGAAG GAGCTGAAGG AGATCAGGGT CTTGGACAAG GCCTTCGGAC AGAATTGAG | 1380 |
| |  K  E  K    E  L  K    E  I  R  V    L  D  K    A  F  G    P  E  L  R | |
| 1381 | AGAGGAATTT TCTAGTAAGT AAACTTGGGT CATGGGTGTG TGGTTCCATC TTAAACACTG | 1440 |
| |  E  E  F    S  (SEQ ID NO:2) | |
| 1441 | CATGTATGTG GGGGAGATG GACCTTGTCT AGCAAGTTAT TGAAATTTGT AGCCAAATCT | 1500 |

Figure 1 – page 2

```
1501  AAGCCAATCT CACATCCAAA GTCATCAAGA AATAAATATT AAATAGTATA AAATGGCATA  1560
1561  GTATGAAAGA TACTGGGTGG GATTTCCAGA GACTAGATTC TGGCCCTGAC CCAGAACTTG  1620
1621  AGAAGCAGCC ACCTCAGCCT CCAGGCCTCT TTTCTTCTCA TCTAGAAAAT CCCACATCAG  1680
1681  TTCTTTGTCT TGTCTGCAAC TCTTTTATGT TCTGAAGCTT TTGTCTTGGC AATTGCTGTA  1740
1741  CAACATTCAT AAAGGACACT ATTACCCTGG AGACCTCACC AATGGGTCAT TGTCTCTCTA  1800
1801  GAACGTGCCA GGCTGTGTTT TGTTTTGCAG CTTCCTTAGT ATCCTTTGTG AGGGCAAAAT  1860
1861  AAAAGGAAGT TAAGGTAAAG ATGAGTGTAT AAGTGGGTGT GTGTGACAGA GAGAGAGGAA  1920
1921  AACAATAAGG GGGAGAGAGA GTCGGGGAGA GAGAGTCGGG GAGAGAGACT CAGAGAGAGA  1980
1981  GACAATGAGA AAGACAGAGA AATAATGAAA AATATATAGT GAGAGAGAGA GCATCAGTGA  2040
2041  GAGAATGTGT GTGCACAGTG CACAGCACAG AGCAGAGACA GAGTAAGAGG CAGTATAAGG  2100
2101  CCAGACATGC CTCATTTAGA TTTTGCATAT ATGGCTTTTT TTTAAAAAAA AAAAAACAAA  2160
2161  ACATTTACCT CTGTTGCTCA TCATCAAAAA GAAATTGACT GCAGAATTTT CTGTGGCAAC  2220
2221  TCCTTGTACA AATGGCCCCA AGAGGCAGGT AGAAAAGGCA TCACATCCAA CAGGACAATG  2280
2281  AACGCATCAA GGTCCGGAAT CACAAAGCAA CATGCTAAGG CCATCTGATT GATGCGTAGC  2340
2341  AGAGCTCAGA CCAGAGCTTT ATCCATAGGC TATTTCACCT GGCCCCAGAG CTGATGCTTG  2400
2401  GCAAAGTGGA TCTTCAGTCT CTCCCTTTGC TCCTTGGTGT GCCCCAAAAC AATTCCCTGT  2460
2461  CCTCCTCCCC AACCCAGGGG ATTTGGGGGA CTGTGTGTCT ACATGTGGGC TCTGGCTGCC  2520
2521  CAGAGGGTCC TGCCCTGCCC ACAGAGAATC CCCCACTTGA CAGCACTCAG GGACCACACC  2580
2581  CAACACTCTA CTTTTGCTCT TCTCTGACCT CTTGAAATGT TCGATTTCTT CCACCCTCTG  2640
2641  TTTTAATGTT GTCTTTGATA AACAAATATG AAATGCTTAT AATCCTTGCC TGTGTCTCAG  2700
2701  CAATATTTGC AATTTAACAT CTGAAGCCAG AAAAAAGCAA TGCTCAGCCT AGAGGTATTG  2760
2761  TTCCCCTATG GTAAAAATGC AGATCATATA ATAGACAGGC AGGGATCTGT ATGAAGATAA  2820
2821  AAACAGAGAA AGCATTCAGT GTTCTTTTTG TGCCAGGCAC TTGGCCAAAG GTTTGCCAAC  2880
2881  TCATTTGCTC CTCATAACAA CCCTATGAGA TCGGTAATAT TATCCTCCTT TTTTAAAGAT  2940
2941  GAGGAGATAG AAACAGAGAG GTTAGTTAAC TTTTTGAAGG TCCCACAGTT AGCATATGGC  3000
3001  AAAGCTAGAT TTGAACCCAG ACAGACTAGT GCAGCATCTG TGCTCTTAAG CAGTAGTTTG  3060
3061  TCTTACAGCT CCTTTAGGCC TTCCTCTAGC CCAACTTACA CCATAAAAGC AACTCCATTT  3120
```

Figure 1 – page 3

| | | | | | | |
|---|---|---|---|---|---|---|
| 3121 | AGTCTACATA | AAACACTTGC | CAAGTCTACA | GTGCCTTGGA | GAAGAAGGGA | GCCATGACTT | 3180 |
| 3181 | CATCAACAAA | GTACCTTTTC | CTAGTCCCTC | TAGATCCCTG | GGAACTCACT | GGGGAAGAGT | 3240 |
| 3241 | CCTTTTCTCT | CAGCTTTGGA | CTTCTTCCAC | TTTGACACTC | CTTTGAGCCA | GTCTGTCTGA | 3300 |
| 3301 | AGTGGCAGCA | AAGAAGAAGC | AGAGGAAGGC | AGCAGGAAGG | GCAGAGGTGG | AACTAGAACC | 3360 |
| 3361 | AGAGAACATC | CCACTCTCAG | GCTGTTACCC | ACATCACCAC | CAGCAGCCTC | TTCCCTGACT | 3420 |
| 3421 | CCCCCACTCC | AGGACCTTCT | TGGAGTTGCC | TGACAACGGG | AAGAGGTTGG | GAGTAGACAA | 3480 |
| 3481 | AACATGGCAG | AGGCATCAGG | AGAGCAAGTG | GTCCTGCTTG | TACCCCAGGA | AGGAATTTCT | 3540 |
| 3541 | CCAGCTTCGA | ATTTTTCACT | CTGAATTTTG | CTCTCACTGG | TCTTTGGTCT | TTGTTGCCAA | 3600 |
| 3601 | TTTCAGTTAA | ACTGGCTTAT | TCTTTGGAAA | AGAATGATAT | TAAACAACAG | AAAAGTTGAT | 3660 |
| 3661 | ATTAAACAGC | CAGTCCTGCA | CCTGGTGTAC | AGGGTACAAG | CTTGGAGGCA | GGGTGGGCGT | 3720 |
| 3721 | GTTTAAGCCT | TCACTAGAAA | CGTGACCTTA | GATCTGTCCC | TTAACCTCTC | TGAGACTCAG | 3780 |
| 3781 | TTTCCTCACT | GATAAAGTGG | GACTCAGAAT | ACCTACCTCA | TGAGATAGCT | GTAAAAAGAA | 3840 |
| 3841 | ATAAATATCC | TGTAAGTTGC | ATACAGATGA | TAAAGCACAA | ACAAGTGTAG | AGTATTTATC | 3900 |
| 3901 | CAAGCTCCAT | GTAGCATGGT | GTTCATTTTG | TGGGCTAATT | CCAGGTGACA | ACCTTACTGG | 3960 |
| 3961 | CAGCGTCACT | TCCTGTGGAT | TTCAGAGGAA | CCTGAAGACA | TTGATGTTGT | AACCACTGCC | 4020 |
| 4021 | TCCAGCTAGA | CAGCTGCGAT | GTTAGTTCAT | TGGTGGTTAA | CTCATTTTCA | GCATTGCTAC | 4080 |
| 4081 | CTGCTTTTGA | TGATATCTGA | TAATAGTTTT | CCAGGGAAAT | TCATCATTGA | AGCCCACCCA | 4140 |
| 4141 | CAATTCCTGA | GTAATGACTC | CACTCTCCTC | CCAGTTGCCC | AAGCAGGAAA | CTGTAGGGGT | 4200 |
| 4201 | GATTTTATCT | TCTCCTTTTC | CTATCAGCTC | AGATCCAATA | GGTACCAGGA | CCTTCAAGGT | 4260 |
| 4261 | AAGGTCTGAA | ATTCAAACCT | GGTATATCTC | TCCCCTCCTC | TGCTTCCACT | GCTGGACCCT | 4320 |
| 4321 | GCTTCCAGTC | CTCATCGAAA | CTTTGGCACA | GACATTCTGA | TTAATCACTT | GATCATCAGT | 4380 |
| 4381 | CTTTCTCAAA | TCCCCTATAC | CAGTCCATTT | TATATCCTCA | AGCCAAGATT | AACTTCCTAC | 4440 |
| 4441 | ACCACAACCC | TGCTTTTGTT | CCTTTTTTTG | TTGTTGCTTG | TGTGGTTTTC | TTTTTTTTTT | 4500 |
| 4501 | TTTTTTTTT | TTTTTTTTTT | TTTTTTGAG | ACAAGGTGGT | CTTGCTCTAC | CACCCAGGCT | 4560 |
| 4561 | AGAGTGCAGA | GGTGTGATCT | TGGCTCACTG | CCAGGAACCA | GAGACCCCAG | CCTCCATTTA | 4620 |
| 4621 | TCCTCCCACC | TCAGTCTGCA | GAGTAGCTGG | GACTGCAGGC | AGGCACATGC | CACCATGCCC | 4680 |
| 4681 | AGCTATTTCA | TGTATTTTAA | TAGAAATGGG | ATTTCCCCAT | GTTGTCCAAG | CTGGTCTCAA | 4740 |

Figure 1 – page 4

```
4741  CCTCCTGCGC TCCAGTGATC CATCCATCAC AGCCTCCCAA AGTGCTGGAA TAACAGGCAT  4800
4801  GAGCCACGGG GCTTGGCCTT TTTGTCATTT TATTCCAAAT ATAAATAAGG GGTTTTCTTT  4860
4861  AACATGATGC TGGAGTCCCA AAATTATGAT TCTATACATG ATTTCTCATT ACTTACAGAA  4920
4921  TTAACTTCAA ACTTTTCCCT CATACTCTCT ACAATCACAC TACTCTCCTT AGAAAATTTG  4980
4981  ATGGGCTTCC CATGACTCTA GCAATGCTTA TATTCCAGGC ATACCTGACA GCTCACTGCT  5040
5041  CAGATTACTT TTCTAAAATG AGATGGGAGA GAAACAGATG TTTGCTCTTT CCAAGAAATT  5100
5101  GATACACATG CTGATTTCTG TGCCTTTTTT ACTTGTTCTT TCCGTAGAAT GTACACCCTC  5160
5161  CACTCTAACA CCCTACTCTA ACCATCCTTG AACACCTATG TAACATCACC TTTATCAGAA  5220
5221  AACTTCTCAG CCAGATACAG AAATCATTCC AATGACCTGA CCTGTGTTCA CACAGAACTC  5280
                                                                   K   L
5281  CAGAACAAGA CCAAGCTGAC AGTGCTGGAA GGAGACATTC TGGATGAGCC ATTCCTGAAG  5340
       Q  N  K   T  K  L   T  V  L   E  G  D   I  L  D   E  P  F  L  K
5341  AGAGCCTGCC AGGACGTCTC GGTCATCATC CACACCGCCT GTATCATTGA TGTCTTCGGT  5400
       R  A  C   Q  D  V   S  V  I   I  H  T   A  C  I   I  D  V  F  G
5401  GTCACTCACA GAGAGTCTAT CATGAATGTC AATGTGAAAG GTATGGTAGG CTGGGGAGGA  5460
       V  T  H   R  E  S   I  M  N  V  N  V  K  (SEQ ID NO:3)
5461  GATGCAGCAA GGTGGGGAAT TAAGGATCAC AAAGAAGGGC AGGAAGGGAA GAGAAGTCCC  5520
5521  TCCACTGAAC ACCTGCTGTG CTCTGGGCCA AGTGCCTTTG CTGATCACTA CGAATAGGAG  5580
5581  AGTTCAAGAC TGCTAACTTT AGTTTTTTAG ATGATAAAAC TAGGACTGAG AGAGGGCAAG  5640
5641  TAACTTGTCC AAGGTCCCCC AGGTAAGTAA GCAGGTAGGA GAGTTAGACT TTAAACTCAT  5700
5701  CCCTGTGTGA CTCCAAAGGC TCTTTCTACT GTGACTCCAA AAGCTCTTTC TACTGTGGTT  5760
5761  CCAATCAAAA GTCAACTAAT TTCTGACTTC AGACTCTTGA TACCCAGACA CCCCTTGCCT  5820
5821  CCCAGGCCAG AAGCAGACCT TGCAGGTGCC ACTGTAGTCA CCATTTTGAA CCTTGTGTGT  5880
5881  AGGCTGATGA AAACATTCAG AGCCCTCCTG CCCACCTCAA ACAAAAGTC CTCTCGAGAG   5940
5941  AACTAGCAAA GCTGGTTCAC AAGGTCTGTC AGGACAGAAT TATCCAGCAC ATGCCTTCCC  6000
6001  ACAATATTTT TTTAACAGTG AGATTTTTCC AGTATCAAGA ATACAGTCTC TTCAGCTCAC  6060
6061  CACAGGGCCT ACTATTCCAG AGCCGTTTTC AGCCAGGTGC CCAAAGTGCA CCCTCATTTA  6120
6121  ATCTTCATCC CTTAAATGCT TGGCGTTTCC TTTCAAAGTA TGGCTTTCCA ACTACCTTAA  6180
6181  ATTCAGACAC ATTTCCTTAA GGAATCTTCT CAGAAATCTC ACCCTCTGAT CTCCAGAGTC  6240
```

Figure 1 – page 5

| | | | | | |
|---|---|---|---|---|---|
|6241|CAGTCTCTTC AGCACCATAG CACCCCAAAC CCCGGCCTGG CCCTCCGCAT TTAGTCTACT|6300|
|6301|CTGACTCTTT TTCCAAAGCA ACCAATTGCT TTTGAGTCTC CAGCACCATA AAAGAAAAAA|6360|
|6361|AAAAACAACT TCCAGTTTCT ACTTACCCAT ACTTCTAAGT ACCCCTGCTG TGCAAGGAGG|6420|
|6421|GTGCTAAGAG TAACCAGTTT TAATTACTAC TTCAACAGCT CCCAAAAGGA GGGGATATGA|6480|
|6481|AATGACAGGG GAAGTGTTAG AGGCATCTGT TTGCTAAAAC CATTATAACT CCCAAGCTTA|6540|
|6541|GAAAATACTT CACAATGTTG GTCATTTCCC CCTTGAAGGT AAACTAACTC CAAATTTTCT|6600|
|6601|CTGCCACAAG ATTAATTTTT GAACACATGA GGCTGTCTTT CCAGAAACTC AAATTGCACA|6660|
|6661|GAGACATTAA AAGGGCTAAG AATACAAAAA TTTGTAAATA AAAATGATCC TTTCCCTAGG|6720|
|6721|AAATTCCTTC CTTCTTCAAG GGAAGGCACT ATGGGTACCT CCATGAGCTT TGCTTCTACA|6780|
|6781|CAGCTCAGGG GAGGCTGCAA GGTCCTCCCA CTGCAGGTGT TACCAGCAGA GGACACACTT|6840|
|6841|CTCTCCCCAG CCCTCCACCA GGCTCCACAG GAAATGCCAG GGCAGGGTTT AAAAGAAGGT|6900|
|6901|TTATCACCTC CACTTTACAT AACCAGGTAA ACAGAGTCAC AGCCAGAATT GGAAGCAGCT|6960|
|6961|TTCCCAGGGA ATGCACAATC AGGAAGAGTG TGGGTTTCCA GCATCTCCCC ACAACCCACT|7020|
|7021|GCTTGCTCAG TGACTCCAGG ATGGTCCTTG TGACAAAGTT TTATTAGAGC CCAGCAAAAT|7080|
|7081|GAGAAAAGTA CCAACAATTT CATATATATT GAAGAGTTTA TATTGCCTAT ATACAATGGT|7140|
|7141|GTATGTGTGT GTGTGATGTG AATTCTTCAA CTGCCCATTT TGCCTAAGGA CTGGAACTGT|7200|
|7201|CCATATTCAC AGAGTATAGC CTCCTGATTT TTTAGATTTT AAATGATCTG ACTTTAATGG|7260|
|7261|TACTGATTAC AAATCATAAT TTGTCAATAC CCTTACTTGG CAAAATAAAA AGTGATAACC|7320|
|7321|CTAGGTCCCT TTCCAAAATT AAAGTACACA CACACACACA TCCATGAAAC CCAAAAGTCT|7380|
|7381|AGAAATTCTT ACTCTCCAGA ACCCACATGT CAGTTTCTCT TCATTTTGGT ATTTTTCTTA|7440|
|7441|TGGCTGTAGT ACGACCAAAT CTCAGACAGA ACCACAGAAG AATGTACCCT GAGTCTGTTA|7500|
|7501|CAACCACCAT ATTTGGGAGT GGGGGGTGGG GCACATAGAT CTGTGTTCGT GGTTGGCACC|7560|
|7561|TCTTAGGGAT ATATCCTGAC AGTGACAATA TGCTCTTCAT GGACAGGTAC CCAGCTCCTG|7620|

```
                                                              G   T   Q   L   L
7621 TTAGAGGCCT GTGTCCAAGC TAGTGTGCCA GTCTTCATCT ACACCAGTAG CATAGAGGTA 7680
      L   E   A   C   V   Q   A   S   V   P   V   F   I   Y   T   S   S   I   E   V
7681 GCCGGGCCCA ACTCCTACAA GGAAATCATC CAGAATGGCC ATGAAGAAGA GCCTCTGGAA 7740
      A   G   P   N   S   Y   K   E   I   I   Q   N   G   H   E   E   E   P   L   E
```

Figure 1 – page 6

```
7741  AACACATGGC CCGCTCCATA CCCACACAGC AAAAAGCTTG CTGAGAAGGC TGTACTGGCG  7800
       N  T  W    P  A  P  Y    P  H  S    K  K  L    A  E  K  A    V  L  A

7801  GCTAACGGGT GGAATCTGAA AAACGGCGGC ACCCTGTACA CTTGTGCCTT ACGACCCATG  7860
       A  N  G    W  N  L  K    N  G  G    T  L  Y    T  C  A  L    R  P  M

7861  TATATCTATG GGAAGGAAG  CCGATTCCTT TCTGCTAGTA TAAACGAGGC CCTGAACAAC  7920
       Y  I  Y    G  E  G  S    R  F  L    S  A  S    I  N  E  A    L  N  N

7921  AATGGGATCC TGTCAAGTGT TGGAAAGTTC TCCACTGTTA ACCCAGTCTA TGTTGGCAAT  7980
       N  G  I    L  S  S    V  G  K  F    S  T  V    N  P  V  Y    V  G  N

7981  GTGGCCTGGG CCCACATTCT GGCCTTGAGG GCCCTGCAGG ACCCCAAGAA GGCCCAAGC   8040
       V  A  W    A  H  I  L    A  L  R    A  L  Q    D  P  K  K    A  P  S

8041  ATCCGAGGAC AGTTCTACTA TATCTCAGAT GACACGCCTC ACCAAAGCTA TGATAACCTT  8100
       I  R  G    Q  F  Y  Y    I  S  D    D  T  P    H  Q  S  Y    D  N  L

8101  AATTACACCC TGAGCAAAGA GTTCGGCCTC CGCCTTGATT CCAGATGGAG CTTTCCTTTA  8160
       N  Y  T    L  S  K  E    F  G  L    R  L  D    S  R  W  S    F  P  L

8161  TCCCTGATGT ATTGGATTGG CTTCCTGCTG GAAATAGTGA GCTTCCTACT CAGGCCAATT  8220
       S  L  M    Y  W  I  G    F  L  L    E  I  V    S  F  L  L    R  P  I

8221  TACACCTATC GACGCCCCTT CAACCGCCAC ATAGTCACAT TGTCAAATAG CGTATTCACC  8280
       Y  T  Y    R  P  P  F    N  R  H    I  V  T    L  S  N  S    V  F  T

8281  TTCTCTTATA AGAAGGCTCA GCGAGATCTG GCGTATAAGC CACTCTACAG CTGGGAGGAA  8340
       F  S  Y    K  K  A  Q    R  D  L    A  Y  K    P  L  Y  S    W  E  E

8341  GCCAAGCAGA AAACGGTGGA GTGGGTTGGT TCCCTTGTGG ACCGGCACAA GGAGCCCTG   8400
       A  K  Q    K  T  V  E    W  V  G    S  L  V    D  R  H  K    E  T  L

8401  AAGTCCAAGA CTCAGTGATT TAAGGATGAC AGAGATGTGC ATGTGGGTAT TGTTAGGAGA  8460
       K  S  K    T  Q    (SEQ ID NO:4)

8461  TGTCATCAAG CTCCACCCTC CTGGCCTCAT ACAGAAAGTG ACAAGGGCAC AAGCTCAGGT  8520

8521  CCTGCTGCCT CCCTTTCATA CAATGGCCAA CTTATTGTAT TCCTCATGTC ATCAAAACCT  8580

8581  GCGCAGTCAT TGGCCCAACA AGAAGGTTTC TGTCCTAATC ATATACCAGA GGAAAGACCA  8640

8641  TGTGGTTTGC TGTTACCAAA TCTCAGTAGC TGATTCTGAA CAATTTAGGG ACTCTTTTAA  8700

8701  CTTGAGGGTC GTTTTGACTA CTAGAGCTCC ATTTCTACTC TTAAATGAGA AAGGATTTCC  8760

8761  TTTCTTTTTA ATCTTCCATT CCTTCACATA GTTTGATAAA AAGATCAATA AATGTTTGAA  8820

8821  TGTTTAATGT GGAGGGAGGT GTGAGTTATG TTAATACATA CTTTCCTCCT TTCTCCTTCT  8880

8881  TTTCCAGGTA TTGCCATCTC CAATTTAGAA GAGTAGCATA AAACCTGGGT TGGGGAGAGG  8940
```

Figure 1 – page 7

```
8941  GCAGAGTAGT GGGAGGGCCA GGAAGGGCGG ATGAAGACTG AATAAGCTCT ACTACCTTTC  9000
9001  AGGCATGTAC AACATGACCT ACATATGACA TATATTATCT TATTTAATAC TCATCAGAAA  9060
9061  CCTATCTGGT GGGGGTGACT AATCCCATTT TACCACTGAG GAAACTTGTT CACAGTCACA  9120
9121  CTAACTGATT AGTGGCTATG CCTGCTACCA GGGAGTTGGC CTTGAAAGTC CTTATCTTTC  9180
9181  CACGGAATCA CGCAGCCTGA ACTGGTCTTG TCAGTGGTAC AGCAGAGCAC TGGAGCATGC  9240
9241  AGTGCCGATA CGTGGAAGAG ACCCATCTCC GTTGGGTTAC CTCCTTCTTG CCCAGTCCCA  9300
9301  TGCAGGGGAC TCTCTAGAAC CCAGGAGAAT CCCTGGGGAG CATCTGGAAG GGTTTGAATG  9360
9361  CCTTAACAAA TGGCCCTGAG CAGGGGTGAG TGAAGCAAAA ATGCCTCCAG CCTCCACCTT  9420
9421  CAATGCCAAT TTCCTTGAAG GTCTCTAGAA CACACCTGGC TATATGTGTG TTAGTCATTC  9480
9481  TGATCATACA TAACCCTGCA TTTCACCCTT TCAAATCACA CAGTGAAGCC ACACCATGGG  9540
9541  TTCCTGGGCA AGTAAAGGGA ACAAGTTTAA ACTTCCCCCA AAATGTGCCT TCTATTCAGC  9600
9601  CCAAGAAGTA AGTCTACTGT CCCACATCCC CAGATTTAAC TGCCTCTCTC TTCATTCTCC  9660
9661  TTCTCTTCTT GAGATCATAT CTTTTCCTCC TTTATTCTTT CATCTCCTTA GCCTCTTTCC  9720
9721  TTCCCTCCAA ATCCCCTTAA ATCACTGGCT CTCTCATTCT TCTCAATTTC CCTGAGGAAA  9780
9781  GGAGGCTAAT CAAGACAAGC TTGGGGACTT CGATGATGAC ATAG  9824   (SEQ ID NO:1)
```

Figure 2 – page 1

```
1     ATGACGGGCT GGAGCTGCCT TGTGACAGGA GCAGGAGGGT TTCTGGGACA GAGGATCATC   60
      M  T  G   W  S  C  L   V  T  G    A  G  G    F  L  G  Q   R  I  I

61    CGCCTCTTGG TGAAGGAGAA GGAGCTGAAG GAGATCAGGG TCTTGGACAA GGCCTTCGGA  120
      R  L  L   V  K  E  K   E  L  K   E  I  R    V  L  D  K   A  F  G

121   CCAGAATTGA GAGAGGAATT TTCTAAACTC CAGAACAAGA CCAAGCTGAC AGTGCTGGAA  180
      P  E  L   R  E  E  F   S  K  L   Q  N  K    T  K  L  T   V  L  E

181   GGAGACATTC TGGATGAGCC ATTCCTGAAG AGAGCCTGCC AGGACGTCTC GGTCATCATC  240
      G  D  I   L  D  E  P   F  L  K   R  A  C    Q  D  V  S   V  I  I

241   CACACCGCCT GTATCATTGA TGTCTTCGGT GTCACTCACA GAGAGTCTAT CATGAATGTC  300
      H  T  A   C  I  I  D   V  F  G   V  T  H    R  E  S  I   M  N  V

301   AATGTGAAAG GTACCCAGCT CCTGTTAGAG GCCTGTGTCC AAGCTAGTGT GCCAGTCTTC  360
      N  V  K   G  T  Q  L   L  L  E   A  C  V    Q  A  S  V   P  V  F

361   ATCTACACCA GTAGCATAGA GGTAGCCGGG CCCAACTCCT ACAAGGAAAT CATCCAGAAT  420
      I  Y  T   S  S  I  E   V  A  G   P  N  S    Y  K  E  I   I  Q  N

421   GGCCATGAAG AAGAGCCTCT GGAAAACACA TGGCCCGCTC CATACCCACA CAGCAAAAAG  480
      G  H  E   E  E  P  L   E  N  T   W  P  A    P  Y  P  H   S  K  K

481   CTTGCTGAGA AGGCTGTACT GGCGGCTAAC GGGTGGAATC TGAAAAACGG CGGCACCCTG  540
      L  A  E   K  A  V  L   A  A  N   G  W  N    L  K  N  G   G  T  L

541   TACACTTGTG CCTTACGACC CATGTATATC TATGGGGAAG GAAGCCGATT CCTTTCTGCT  600
      Y  T  C   A  L  R  P   M  Y  I   Y  G  E    G  S  R  F   L  S  A

601   AGTATAAACG AGGCCCTGAA CAACAATGGG ATCCTGTCAA GTGTTGGAAA GTTCTCCACT  660
      S  I  N   E  A  L  N   N  N  G   I  L  S    S  V  G  K   F  S  T

661   GTTAACCCAG TCTATGTTGG CAATGTGGCC TGGGCCCACA TTCTGGCCTT GAGGGCCCTG  720
      V  N  P   V  Y  V  G   N  V  A   W  A  H    I  L  A  L   R  A  L

721   CAGGACCCCA AGAAGGCCCC AAGCATCCGA GGACAGTTCT ACTATATCTC AGATGACACG  780
      Q  D  P   K  K  A  P   S  I  R   G  Q  F    Y  Y  I  S   D  D  T

781   CCTCACCAAA GCTATGATAA CCTTAATTAC ACCCTGAGCA AAGAGTTCGG CCTCCGCTT   840
      P  H  Q   S  Y  D  N   L  N  Y   T  L  S    K  E  F  G   L  R  L

841   GATTCCAGAT GGAGCTTTCC TTTATCCCTG ATGTATTGGA TTGGCTTCCT GCTGGAAATA  900
      D  S  R   W  S  F  P   L  S  L   M  Y  W    I  G  F  L   L  E  I

901   GTGAGCTTCC TACTCAGGCC AATTTACACC TATCGACGGC CCTTCAACCG CCACATAGTC  960
      V  S  F   L  L  R  P   I  Y  T   Y  R  P    P  F  N  R   H  I  V

961   ACATTGTCAA ATAGCGTATT CACCTTCTCT TATAAGAAGG CTCAGCGAGA TCTGGCGTAT 1020
      T  L  S   N  S  V  F   T  F  S   Y  K  K    A  Q  R  D   L  A  Y

1021  AAGCCACTCT ACAGCTGGGA GGAAGCCAAG CAGAAAACGG TGGAGTGGGT TGGTTCCCTT 1080
      K  P  L   Y  S  W  E   E  A  K   Q  K  T    V  E  W  V   G  S  L
```

Figure 2 – page 2

```
1081    GTGGACCGGC ACAAGGAGAC CCTGAAGTCC AAGACTCAGT GA 1122 (SEQ ID NO:5)
         V    D    R    H    K    E    T    L    K    S    K    T    Q  (SEQ ID NO:6)
```

HSD3B1 SEQUENCE VARIANTS

CROSS-REFERENCE TO RELATED APPLICATIONS

This application claims priority to U.S. Provisional Patent Application Ser. No. 60/697,212, filed on Jul. 7, 2005, the entire contents of which are hereby incorporated by reference.

STATEMENT AS TO FEDERALLY SPONSORED RESEARCH

This invention was made with government support under grant nos. GM61388, GM28157-24, and GM35720-19, awarded by the National Institutes of Health. The government has certain rights in the invention.

TECHNICAL FIELD

This document relates to HSD3B1 nucleic acid and amino acid sequence variants.

BACKGROUND

The enzyme hydroxy-delta-5-steroid dehydrogenase, 3 beta- and steroid delta-isomerase 1 (HSD3B1; also referred to as HSD3B and HSDB3) catalyzes the conversion of 3-hydroxy-5-ene-steroids [e.g., dehydroepiandrosterone (DHEA) and pregnenolone] to 3-oxo-4-ene-steroids (androstenedione and progesterone, respectively). A single, dimeric HSD3B1 protein contains both enzyme activities. The HSD3B1 gene is expressed predominantly in mammary gland tissue, and also is expressed in placenta and skin. At the subcellular level, HSD3B1 is located in the endoplasmic reticulum and the mitochondrial membrane. During human pregnancy, the placental enzyme catalyzes conversion of pregnenolone to progesterone, which maintains the uterus in a quiescent state. Near term, however, the fetal zone adrenal gland produces large amounts (200 mg/day) of DHEA. Because the fetal adrenal gland lacks significant HSD3B1 activity, the placental enzyme converts the fetal DHEA to androstenedione. Androstenedione in turn is converted by placental aromatase and 17-hydroxysteroid dehydrogenase to estradiol, which participates in the cascade of events that initiates labor in humans. Other substrates for HSD3B1 include 17-hydroxypregnenolone and androst-5-ene-3-B,17B-diol. The HSD3B1 enzyme also is selectively expressed in human breast tumors, prostate tumors, and choriocarcinomas, where it catalyzes the first step in the conversion of circulating DHEA to, estradiol or testosterone to promote tumor growth.

Congenital deficiency of HSD3B1 activity causes severe depletion of steroid formation and frequently is lethal early in life. The classical form of this disease includes the association of severe salt-losing adrenal insufficiency and ambiguity of external genitalia in both sexes.

SUMMARY

This document is based on the discovery of sequence variants that occur in both coding and non-coding regions of HSD3B1 nucleic acids. Certain HSD3B1 nucleotide sequence variants encode HSD3B1 enzymes that are associated with individual differences in enzymatic activity. Other HSD3B1 sequence variants in non-coding regions of the HSD3B1 nucleic acid may alter regulation of transcription and/or splicing of the HSD3B1 nucleic acid. Discovery of these sequence variants allows individual differences in the biosynthesis of steroids in humans to be assessed based on the presence or absence of one or more such variants. The presence of these sequence variants also may affect pathogenesis of steroid related diseases, such as prostate cancer, and thus may be useful to indicate prognosis.

In one aspect, this document features an isolated nucleic acid containing a variant HSD3B1 nucleic acid sequence, wherein said variant HSD3B1 nucleic acid sequence is selected from the group consisting of: (a) at least a ten-nucleotide sequence of SEQ ID NO: 1, wherein the sequence includes nucleotide position 735 of SEQ ID NO: 1, with the proviso that the nucleotide at position 735 is thymine; or (b) at least a ten-nucleotide sequence of SEQ ID NO: 1, wherein the sequence includes nucleotide position 1083 of SEQ ID NO: 1, with the proviso that the nucleotide at position 1083 is adenine; or (c) at least a ten-nucleotide sequence of SEQ ID NO: 1, wherein the sequence includes nucleotide position 5254 of SEQ ID NO: 1, with the proviso that the nucleotide at position 5254 is cytosine; or (d) at least a ten-nucleotide sequence of SEQ ID NO: 1, wherein the sequence includes nucleotide position 5296 of SEQ ID NO: 1, with the proviso that the nucleotide at position 5296 is thymine; or (e) at least a ten-nucleotide sequence of SEQ ID NO: 1, wherein the sequence includes nucleotide position 5417 of SEQ ID NO: 1, with the proviso that the nucleotide at position 5417 is thymine; or (f) at least a ten-nucleotide sequence of SEQ ID NO: 1, wherein the sequence includes nucleotide position 8020 of SEQ ID NO: 1, with the proviso that the nucleotide at position 8020 is adenine; or (g) at least a ten-nucleotide sequence of SEQ ID NO: 1, wherein the sequence includes nucleotide position 8229 of SEQ ID NO: 1, with the proviso that the nucleotide at position 8229 is cytosine; or (h) at least a ten-nucleotide sequence of SEQ ID NO: 1, wherein the sequence includes nucleotide position 8235 of SEQ ID NO: 1, with the proviso that the nucleotide at position 8235 is adenine; or (i) at least a ten-nucleotide sequence of SEQ ID NO: 1, wherein the sequence includes nucleotide position 8313 of SEQ ID NO: 1, with the proviso that the nucleotide at position 8313 is adenine; or (j) the complement of (a), (b), (c), (d), (e), (f), (g), (h), or (i).

In another aspect, this document features an isolated nucleic acid encoding an HSD3B1 polypeptide, wherein the polypeptide contains an HSD3B1 amino acid sequence variant relative to the amino acid sequence of SEQ ID NO:6, and wherein the amino acid sequence variant is at a residue selected from the group consisting of 96 and 242. The amino acid sequence variant can be a phenylalanine at residue 96 or an asparagine at residue 242.

This document also features an isolated HSD3B1 polypeptide, wherein the polypeptide contains an HSD3B1 amino acid sequence variant relative to the amino acid sequence of SEQ ID NO:6, wherein the amino acid sequence variant is at a residue selected from the group consisting of 96 and 242. The amino acid sequence variant can be a phenylalanine at residue 96 or an asparagine at residue 242.

In addition, this document features a method for determining an HSD3B1 genotype. The method can comprise: a) providing a nucleic acid sample from a subject, and b) screening the nucleic acid sample for one or more genetic markers in linkage disequilibrium with an HSD3B1 allele. The HSD3B1 allele can be selected from the group consisting of a C-515T allele, an A235G allele, a C287T allele, a G724A allele, a T856C allele, or an A1100C allele.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1 shows the nucleotide sequence of the reference HSD3B1 gene (SEQ ID NO: 1) and the amino acid sequence of the reference HSD3B1 polypeptide (SEQ ID NOs:2, 3, and 4). Exons are depicted in bold type and non-coding sequences are in regular type. Positions of single nucleotide polymorphisms (SNPs) are circled, as are the positions of amino acid changes that result from the SNPs. Primers are underlined, and start and stop codons are double-underlined. The translation initiation codon begins at nucleotide 1250 of SEQ ID NO: 1. Exon 1 contains nucleotides 971 to 1035 of SEQ ID NO:1. Intron 1 contains nucleotides 1036 to 1164 of SEQ ID NO:1. Exon 2 contains nucleotides 1165 to 1394 of SEQ ID NO:1. Intron 2 contains nucleotides 1395 to 5275 of SEQ ID NO:1. Exon 3 contains nucleotides 5276 to 5440 of SEQ ID NO:1. Intron 3 contains nucleotides 5441 to 7606 of SEQ ID NO:1. Exon 4 contains nucleotides 7607 to 8820 of SEQ ID NO:1.

FIG. 2 shows the sequence of the open reading frame (SEQ ID NO:5) of the reference HSD3B1. FIG. 2 also shows the reference amino acid sequence (SEQ ID NO:6) of the encoded HSD3B1 polypeptide. Positions of cSNPs are circled, as are the positions of amino acid changes that result from the cSNPs. Start and stop codons are double-underlined.

DETAILED DESCRIPTION

Figure 3:
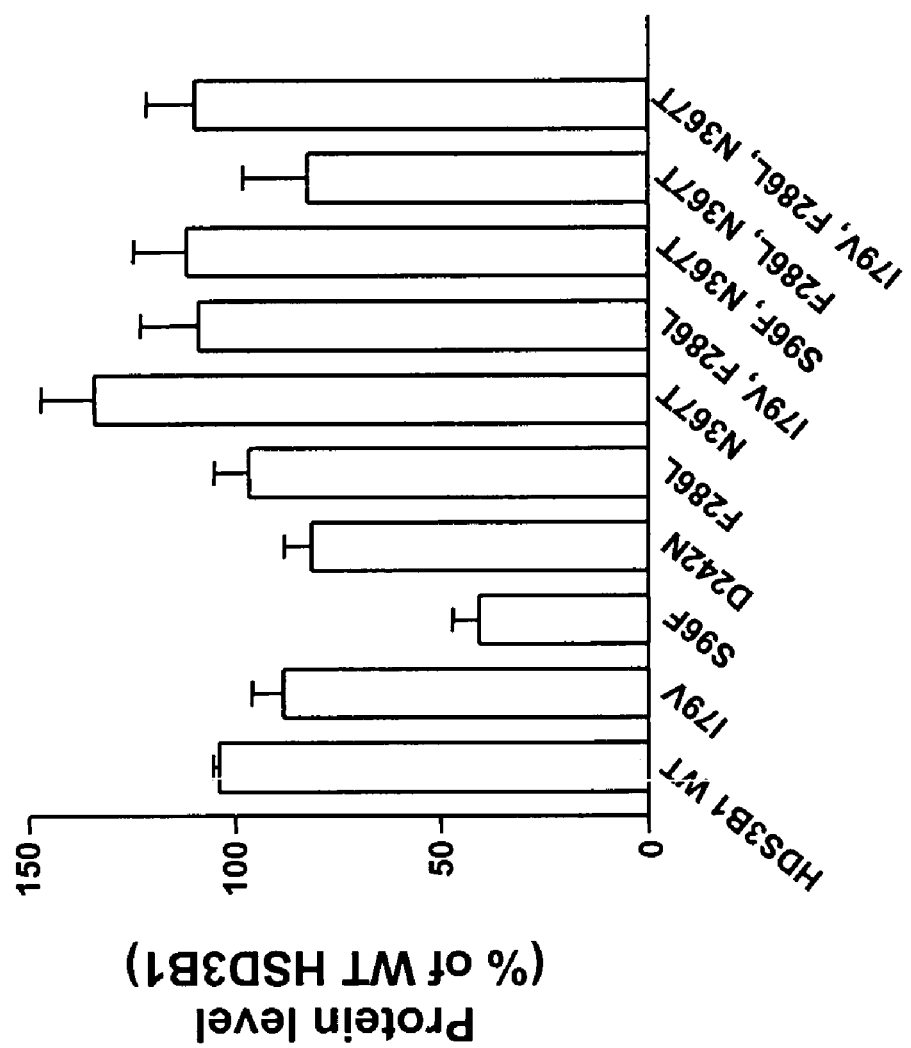
FIG. 3 is a graph plotting protein levels of HSD3B1 allozymes as determined by Western blotting of COS-1 cell extracts. Levels are shown as % WT HDS3B1.

This document discloses HSD3B1 nucleotide and amino acid sequence variants. HSD3B1 is an enzyme involved in steroid synthesis. For example, HSD3B1 catalyzes the oxidative conversion of DHEA to androstenedione and pregnenolone to progesterone. Other substrates for HSD3B1 include 17-hydroxypregnenolone and androst-5-ene-3-B, 17B-diol. Genetically-based variations in HSD3B1 activity that lead to altered levels of HSD3B1 or altered HSD3B1 activity may be important for determining the ability of a subject to synthesize steroids. In addition, since HSD3B1 variations also may affect pathogenesis of steroid related diseases (e.g., prostate cancer), the presence or absence of such variants may be useful to predict prognosis.

Nucleic Acid Molecules

The isolated nucleic acids provided herein can include an HSD3B1 nucleic acid sequence. The HSD3B1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-HSD3B1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids provided herein are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., 150, 200, 250, 300, 350, 400, 450, 500, 750, or 1000 nucleotides in length). Nucleic acids can be in a sense or antisense orientation, can be complementary to the HSD3B1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) Bioorgan. Med. Chem. 4(1):5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in an HSD3B1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference HSD3B1 nucleic acid sequence is provided in FIG. 1 (SEQ ID NO:1) and also can be found in GenBank (see, e.g., Accession No. NT_004754). The reference HSD3B1 cDNA including the HSD3B1 ORF is provided in FIG. 2 (SEQ ID NO:5), as is the corresponding reference HSD3B1 amino acid sequence (SEQ ID NO:6). The mRNA and amino acid reference sequences also can be found in GenBank (see, e.g., Accession No. NM_000862). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences can be designated as "−X" relative to the "A" in the translation initiation codon; positions of nucleotide sequence variants in the coding sequence and 3' untranslated sequence can be designated as "+X" or "X" relative to the "A" in the translation initiation codon. Nucleotide sequence variants that occur in introns can be designated as "+X" or "X" relative to the "G" in the splice donor site (GT) or as "−X" relative to the "G" in the splice acceptor site (AG).

In some embodiments, an HSD3B1 nucleotide sequence variant encodes an HSD3B1 polypeptide having an altered amino acid sequence. The term "polypeptide" refers to a chain of at least four amino acid residues (e.g., 4-8, 9-12, 13-15, 16-18, 19-21, 22-50, 50-100, 100-150, 150-200, 200-250, 250-300, 300-350 residues, or a full-length HSD3B1 polypeptide). HSD3B1 polypeptides may or may not have HSD3B1 catalytic activity, or may have altered activity relative to the reference HSD3B1 polypeptide. Polypeptides that do not have activity or have altered activity can be useful for diagnostic purposes (e.g., for producing antibodies having specific binding affinity for variant HSD3B1 polypeptides).

Corresponding HSD3B1 polypeptides, irrespective of length, that differ in amino acid sequence are herein referred to as allozymes. For example, an HSD3B1 nucleic acid sequence that includes a guanine at position 235 relative to the adenine in the translation initiation codon (i.e., nucleotide 5365 of SEQ ID NO:1 or nucleotide 235 of SEQ ID NO:5) encodes an HSD3B1 polypeptide having a valine at amino acid residue 79. This polypeptide (Ile79Val) would be considered an allozyme with respect to the reference HSD3B1 polypeptide that contains an isoleucine at amino acid residue 79. Additional non-limiting examples of HSD3B1 sequence variants that alter amino acid sequence include variants at nucleotides 287, 724, 856, and 1100 relative to the adenine in the translation initiation codon (i.e., positions 5417, 8020, 8152, and 8396 of SEQ ID NO:1, respectively, or positions 287, 724, 856, and 1100 of SEQ ID NO:5, respectively). For example, an HSD3B1 nucleic acid molecule can include a thymine at nucleotide 287 and encode an HSD3B1 polypeptide having a phenylalanine at amino acid residue 96 in place of a serine residue (Ser96Phe); an adenine at nucleotide 724 and encode an HSD3B1 polypeptide having an asparagine at amino acid residue 242 in place of an aspartic acid residue (Asp242Asn); a cytosine at nucleotide 856 and encode an HSD3B1 polypeptide having a leucine at amino acid residue 286 in place of a phenylalanine (Phe286Leu); or a cytosine at nucleotide 1100 and encode an HSD3B1 polypeptide having a threonine at amino acid 367 in place of an asparagine residue (Asn367Thr).

HSD3B1 allozymes as described above are encoded by a series of HSD3B1 alleles. These alleles represent nucleic acid sequences containing sequence variants, typically multiple sequence variants, within coding and non-coding sequences. Representative examples of single nucleotide variants are described herein. Table 3 sets out a series of HSD3B1 alleles that encode HSD3B1. Some alleles are commonly observed, i.e., have allele frequencies >1%, such as the allele having a thymine at nucleotide 1012 in place of a cytosine. The relatively large number of alleles and allozymes for HSD3B1 indicates the potential complexity of HSD3B1 pharmacogenetics. Such complexity emphasizes the need for determining single nucleotide variants, (i.e., single nucleotide polymorphisms, SNPs) as well as complete HSD3B1 haplotypes (i.e., the set of alleles on one chromosome or a part of a chromosome) of patients.

Certain HSD3B1 nucleotide sequence variants do not alter the amino acid sequence. Such variants, however, could alter regulation of transcription as well as MRNA stability. HSD3B1 variants can occur in intron sequences, for example, within introns 1 or 2. In particular, the nucleotide sequence variant can include an adenine substitution at nucleotide 48 of intron 1 (i.e., nucleotide 1083 of SEQ ID NO:1), a thymine substitution at nucleotide 56 of intron 2 (i.e., nucleotide 1450 of SEQ ID NO:1), or an cytosine substitution at nucleotide −22 of intron 2 (i.e., nucleotide 5254 of SEQ ID NO:1).

HSD3B1 nucleotide sequence variants that do not change the amino acid sequence also can be within an exon or in 5' or 3' untranslated sequences. Exon 3 sequence variants can, for example, include a thymine substitution at nucleotide 166 relative to the adenine in the translation initiation codon (i.e., nucleotide 5296 of SEQ ID NO:1 or nucleotide 166 of SEQ ID NO:5), a thymine substitution at nucleotide 228 (i.e., nucleotide 5358 of SEQ ID NO:1 or nucleotide 228 of SEQ ID NO:5), or an adenine substitution at nucleotide 270 (i.e., nucleotide 5400 of SEQ ID NO:1 or nucleotide 270 of SEQ ID NO:5). Exon 4 sequence variants can include a cytosine substitution at nucleotide 933 (i.e., nucleotide 8229 of SEQ ID NO: 1 or nucleotide 933 of SEQ ID NO:5), an adenine substitution at nucleotide 939 (i.e., nucleotide 8235 of SEQ ID NO:1 or nucleotide 939 of SEQ ID NO:5), a thymine substitution at nucleotide 1012 (i.e., nucleotide 8308 of SEQ ID NO:1 or nucleotide 1012 of SEQ ID NO:5), or an adenine substitution at nucleotide 1017 (i.e., nucleotide 8313 of SEQ ID NO:1 or nucleotide 1017 of SEQ ID NO:5). Nucleotide sequence variants in the 5' flanking region can include a thymine substitution at nucleotide −515 or a cytosine substitution at nucleotide −365 (i.e., nucleotides 735 or 885 of SEQ ID NO:1, respectively).

In some embodiments, an HSD3B1 nucleic acid molecule can consist essentially of at least ten (e.g., at least 12, at least 15, at least 18, at least 20, or at least 25) contiguous nucleotides of an HSD3B1 reference sequence (e.g., SEQ ID NO:1 or SEQ ID NO:5). Such nucleic acids can contain one or more variant positions, with the proviso that the nucleotides at those positions are variant nucleotides as disclosed herein in Table 3, for example. An HSD3B1 nucleic acid "consisting essentially of" a particular sequence has the basic and novel characteristic that it can be used to distinguish, based upon hybridization, a nucleic acid having a sequence that contains a variant from a corresponding nucleic acid having a sequence that does not contain the variant (e.g., a wild type sequence). Such nucleic acid molecules can include additional sequences or labels (e.g., a tag or a fluorescent label as disclosed herein), provided that such additions do not affect the basic and novel characteristic of the nucleic acid molecules.

In some embodiments, an HSD3B1 nucleic acid sequence can have at least 90% (e.g., 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity with a region of SEQ ID NO:1 or SEQ ID NO:5. The region of SEQ ID NO:1 or SEQ ID NO:5 can be at least ten nucleotides in length (e.g., 10, 15, 20, 50, 60, 70, 75, 100, 150 or more nucleotides in length). For example, a nucleic acid can include an HSD3B1 nucleic acid sequence with at least 90% identity to nucleotides 100 to 200, 150 to 250, 200 to 300, 250 to 350, 650 to 750, 700 to 800, 800 to 900, 850 to 950, 900 to 1000, 950 to 1050, 975 to 1075, 1000 to 1100, or 1020 to 1120 of SEQ ID NO:5. For example, an HDS3B1 nucleic acid sequence can have a thymine at nucleotide 166, a thymine at nucleotide 228, a guanine at nucleotide 235, an adenine at nucleotide 270, a thymine at nucleotide 287, an adenine at nucleotide 724, a cytosine at nucleotide 856, a cytosine at nucleotide 933, an adenine at nucleotide 939, a thymine at nucleotide 1012, an adenine at nucleotide 1017, or a cytosine at nucleotide 1100, and combinations thereof, wherein the numbering of the positions is with respect to the numbering of SEQ ID NO:5.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 969 nucleotides from the target sequence aligned with a region of the sequence set forth in SEQ ID NO: 1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900÷969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid containing an HSD3B1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12(9):1; Guatelli et al. (19980 *Proc. Natl. Acad. Sci. USA* 87:1874-1878; and Weiss (1991) *Science*, 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, the reference sequences depicted in FIGS. 1 or 2 can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

HSD3B1 Polypeptides

The isolated HSD3B1 polypeptides provided herein can include an amino acid sequence variant relative to the reference HSD3B1 (FIG. 2, GenBank Accession No. NM_000862). The term "isolated" with respect to an HSD3B1 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

The HSD3B1 polypeptides provided herein can include variants at one or more of amino acid residues 79, 96, 242, 286, and 367. In particular, a valine residue can be substituted at position 79, a phenylalanine residue at position 96, an asparagine residue at position 242, a leucine residue at position 286, or a threonine residue at position 367. In some embodiments, activity of HSD3B1 polypeptides is altered relative to the reference HSD3B1. Certain HSD3B1 allozymes can have reduced activity, while other allozymes can have activity that is comparable to the reference HSD3B1. Other allozymes can have increased activity relative to the reference HSD3B1. Activity of HSD3B1 polypeptides can be assessed in vitro. For example, the methods described by Thomas et al. (see, e.g., *J. Biol. Chem.* (2002) 277:42795-42801 and *J. Biol. Chem.* (2003) 278:35483-35490) can be used to measure HSD3B1 dehydrogenase or isomerase activity. Briefly, an HSD3B1 preparation (e.g., a purified enzyme preparation) can be incubated with a substrate such as DHEA, pregnenolone, or 17α-hydroxypregnenolone in the presence of $NAD^+$, and dehydrogenase activity can be measured as absorbance at 340 nm due to NADH production. Alternatively, an HSD3B1 preparation can be incubated with a substrate such as 5-androstene-3,17-dione in the presence of NADH, and isomerase activity can be measured as absorbance at 241 nm due to androstenedione formation.

Other biochemical properties of allozymes, such as apparent $K_m$ values, also can be altered relative to the reference HSD3B1. Apparent $K_m$ values can be calculated using, for example, the method of Wilkinson with a computer program written by Cleland. Wilkinson (1961) *Biochem. J*, 80:324-332; and Cleland (1963) *Nature* 198:463-365.

Isolated polypeptides can be obtained, for example, by extraction from a natural source (e.g., mammary gland tissue), chemical synthesis, or by recombinant production in a host cell. To recombinantly produce HSD3B1 polypeptides, a nucleic acid encoding an HSD3B1 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to an HSD3B1 nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express HSD3B1 variant polypeptides. For example, BL-21 cells can be transformed with a pGEX vector containing an HSD3B1 nucleic acid sequence. The transformed bacteria can be grown exponentially and then stimulated with isopropylthiogalactopyranoside (IPTG) prior to harvesting. In general, the HSD3B1-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed HSD3B1 polypeptide can be released from the GST moiety.

In eukaryotic host cells, a number of viral-based expression systems can be utilized to express HSD3B1 variant polypeptides. A nucleic acid encoding a polypeptide can be cloned into, for example, a baculoviral vector such as pBlueBac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides can be identified by standard methodology. Alternatively, a nucleic acid encoding a polypeptide can be introduced into a SV40, retroviral, or vaccinia based viral vector and used to infect suitable host cells.

Eukaryotic cell lines that stably express HSD3B1 variant polypeptides can be produced using expression vectors with the appropriate control elements and a selectable marker. For example, the eukaryotic expression vector pCR3.1 (Invitrogen, San Diego, Calif.) and p91023(B) (see Wong et al. (1985) *Science* 228:810-815) or modified derivatives thereof are suitable for expression of HSD3B1 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (Invitrogen) and then transcribed and translated in vitro using wheat germ extract or rabbit reticulocyte lysate.

HSD3B1 variant polypeptides can be purified using known chromatographic methods including ion exchange and gel filtration chromatography. See, for example, Caine et al., *Protein Expr. Purif.* (1996) 8(2):159-166. HSD3B1 polypeptides can be "engineered" to contain a tag sequence describe herein that allows the polypeptide to be purified (e.g., captured onto an affinity matrix). Immunoaffinity chromatography also can be used to purify HSD3B1 polypeptides.

Non-Human Mammals

This document also features non-human mammals that include HSD3B1 nucleic acids provided herein, as well as progeny and cells of such non-human mammals. Non-human mammals include, for example, rodents such as rats, guinea pigs, and mice, and farm animals such as pigs, sheep, goats, horses, and cattle. Non-human mammals can express an HSD3B1 variant nucleic acid in addition to an endogenous HSD3B1 (e.g., a transgenic non-human that includes an HSD3B1 nucleic acid randomly integrated into the genome of the non-human mammal). Alternatively, an endogenous HSD3B1 nucleic acid can be replaced with an HSD3B1 variant nucleic acid as provided herein by homologous recombination. See, Shastry (1998) *Mol. Cell Biochem.,* 181(1-2): 163-179, for a review of gene targeting technology.

In one embodiment, non-human mammals are produced that lack an endogenous HSD3B1 nucleic acid (i.e., a knockout), and then an HSD3B1 variant nucleic acid is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclear of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous HSD3B1 nucleic acid. That is, cultured ES cells can be transformed with a knockout construct and cells selected in which the HSD3B1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning A Laboratory Manual,* second edition, Cold Spring Harbor Press, Plainview; N.Y., 1989.

To generate a knockout animal, ES cells having at least one inactivated HSD3B1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated HSD3B1 allele. If the original ES cell was heterozygous for the inactivated HSD3B1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the HSD3B1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals. For example, fetal fibroblasts can be genetically modified such that they contain an inactivated endogenous HSD3B1 gene and express an HSD3B1 nucleic acid, and then fused with enucleated oocytes. After activation of the oocytes, the eggs are cultured to the blastocyst stage, and implanted into a recipient. See, Cibelli et al. (1998) *Science* 280:1256-1258. Adult somatic cells, including, for example, cumulus cells and mammary cells, can be used to produce animals such as mice and sheep, respectively. See, for example, Wakayama et al. (1998) *Nature* 394:369-374; and Wilmut et al. (1997) *Nature* 385:810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al., supra.

Non-human mammals such as mice can be used, for example, to screen toxicity of compounds that are substrates for HSD3B1, drugs that alter HSD3B1 activity, or for carcinogenesis. For example, HSD3B1 activity or toxicity can be assessed in a first group of such non-human mammals in the presence of a compound, and compared with HSD3B1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting HSD3B1 Sequence Variants

HSD3B1 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods.

Genomic DNA generally is used in the analysis of HSD3B1 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizards® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the HSD3B1 gene can be amplified then directly sequenced. Dye primer sequencing can be used to increase the accuracy of detecting heterozygous samples.

Nucleic acid molecules provided herein can be used to detect variant HSD3B1 sequences. For example, allele specific hybridization can be used to detect sequence variants, including complete haplotypes of a subject (e.g., a mammal such as a human). See, Stoneking et al. (1991) *Am. J Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For HSD3B1 sequence variants that do not alter a common restriction site, mutagenic primers can be designed that introduce a restriction site when the variant allele is present or when the wild type allele is present. A portion of HSD3B1 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of HSD3B1 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele (e.g., an HSD3B1 nucleic acid as provided herein). Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) *Genome* 11:163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, HSD3B1 variants can be detected by antibodies that have specific binding affinity for variant HSD3B1 polypeptides. Variant HSD3B1 polypeptides can be produced in various ways, including recombinantly, as discussed above. Host animals such as rabbits, chickens, mice, guinea pigs, and rats can be immunized by injection of an HSD3B1 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using an HSD3B1 variant polypeptide and standard hybridoma technology. In particular, monoclonal antibodies can be obtained by any technique that provides for the production of antibody molecules by continuous cell lines in culture such as described by Kohler et al. (1975) *Nature* 256:495, the human B-cell hybridoma technique (Kosbor et al. (1983) *Immunology Today*, 4:72; Cote et al. (1983) *Proc. Natl. Acad. Sci USA* 80:2026), and the EBV-hybridoma technique (Cole et al. (1983) *Monoclonal Antibodies and Cancer Therapy*, Alan R. Liss, Inc., pp. 77-96. Such antibodies can be of any immunoglobulin class including IgG, IgM, IgE, IgA, IgD and any subclass thereof. The hybridoma producing the monoclonal antibodies can be cultivated in vitro and in vivo.

Antibody fragments that have specific binding affinity for an HSD3B1 variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., *Science,* 246:1275 (1989). Once produced, antibodies or fragments thereof are tested for recognition of HSD3B1 variant polypeptides by standard immunoassay methods including ELISA techniques, radioimmunoassays and Western blotting. See, *Short Protocols in Molecular Biology*, Chapter 11, Green Publishing Associates and John Wiley & Sons, edited by Ausubel et al., 1992.

Methods

Given the disclosure provided herein, it is possible to determine steroid synthesis status of a subject (e.g., a mammal such as a human). "Steroid synthesis status" refers to the ability of a subject to convert a 3-hydroxy-5-ene-steroid (e.g., DHEA) to a 3-oxo-4-ene-steroid (e.g., androstenedione). Steroid synthesis status of a subject can be determined by, for example, measuring the level of HSD3B1 activity in the subject using, for example, the methods described herein. Alternatively, steroid synthesis status can be evaluated by determining whether an HSD3B1 nucleic acid sequence of a subject contains one or more variants (e.g., one or more variants that are correlated with increased or decreased HSD3B1 activity). A variant that results in decreased or increased HSD3B1 activity can be said to result in "reduced" or "enhanced" steroid synthesis status, respectively. In some embodiments, the variant profile of a subject can be used to determine the steroid synthesis status of the subject.

"Variant profile" refers to the presence or absence of a plurality (e.g., two or more) of HSD3B1 nucleotide sequence variants or HSD3B1 amino acid sequence variants. For example, a variant profile can include the complete HSD3B1 haplotype of the mammal (e.g., see Tables 6-9) or can include the presence or absence of a set of particular non-synonymous SNPs (e.g., single nucleotide substitutions that alter the amino acid sequence of an HSD3B1 polypeptide). In one embodiment, the variant profile includes detecting the presence or absence of two or more non-synonymous SNPs (e.g., 2, 3, or 4 non-synonymous SNPs) described herein. There may be ethnic-specific pharmacogenetic variation, as certain of the nucleotide and amino acid sequence variants described herein were detected solely in African-American, Caucasian-American, Han Chinese-American, or Mexican-American subjects. In addition, the variant profile can include detecting the presence or absence of any type of HSD3B1 SNP together with any other HSD3B1 SNP (e.g., a polymorphism pair or a group of polymorphism pairs). Such polymorphism pairs include, without limitation, the pairs described in Tables 5 and 6. Further, a variant profile can include detecting the presence or absence of any HSD3B1 SNP together with any SNP from one or more other genes involved in steroid synthesis.

Steroid synthesis activity of an enzyme such as HSD3B1 can be measured using, for example, in vitro methods such as those described herein. As used herein, the term "reduced steroid synthesis status" refers to a decrease (e.g., a 5%, 10%, 15%, 20%, 25%, 30%, 40%, 50%, 60%, 70%, 75%, 80%, 90%, 95%, or 100% decrease) in steroid synthesis activity (e.g., HSD3B1 activity) of a subject, as compared to a control level of steroid synthesis activity. Similarly, the term "enhanced steroid synthesis status" refers to an increase (e.g., a 5%, 10%, 15%, 20%, 25%, 30%, 40%, 50%, 60%, 70%, 75%, 80%, 90%, 95%, 100%, or more than 100% increase) in steroid synthesis activity of a subject, as compared to a control level of steroid synthesis activity. A control level of steroid synthesis activity can be, for example, an average level of steroid synthesis activity in a population of individuals. In one embodiment, the population includes individuals that do not contain particular HSD3B1 nucleotide sequence variants or particular HSD3B1 amino acid sequence variants (e.g., particular variants that affect steroid synthesis status). Alternatively, a control level of steroid synthesis activity can refer to the level of steroid synthesis activity in a control subject (e.g., a subject that does not contain an HSD3B1 nucleic acid containing a variant).

In some embodiments, evaluation of steroid synthesis status can be used in diagnostic assays. In further embodiments, steroid synthesis status can be linked to predisposition to a particular condition. Alterations in steroid synthesis may lead to altered hormone levels, which in turn can result in conditions such as polycystic ovary syndrome (Carbunaru (2004) *J. Clin. Endocrinol. Metab.* 89:783-794) or hereditary and sporadic prostate cancer (Chang (2002) *Cancer Res.* 62:1784-1789), for example. Predisposition to such a condition can be determined based on the presence or absence of a single HSD3B1 sequence variant or based on a variant profile.

Determination of steroid synthesis status and predisposition to particular clinical conditions can include identification of genetic markers (e.g., polymorphisms) in linkage disequilibrium with particular HSD3B1 alleles. Although such markers may not be relevant from a functional perspective (i.e., may not directly affect function of HSD3B1), their presence can be predictive of functional/clinically relevant polymorphisms. Thus, this document also provides methods for detecting a genotype by screening for genetic markers in linkage disequilibrium with particular HSD3B1 alleles. The methods can include providing a nucleic acid sample from a subject (e.g., a human subject), and screening the sample for one or more markers in linkage disequilibrium with a particular HSD3B1 allele. For example, a method can include screening for markers in linkage disequilibrium with a SNP at nucleotide 235, 287, 724, 856, or 1100 relative to the adenine in the translation initiation codon (nucleotide 5365, 5417, 8020, 8152, or 8395 respectively, of SEQ ID NO:1). A method can include screening for genetic markers in linkage disequilibrium with a SNP at nucleotide −515 relative to the adenine in the translation initiation codon (i.e., nucleotide 735 of SEQ ID NO:1). Methods also can include screening for genetic markers in linkage disequilibrium with any of the other SNPs shown in Table 3.

Articles of Manufacture

Also provided herein are articles of manufacture, which can include populations of isolated HSD3B1 nucleic acid molecules or HSD3B1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different HSD3B1 nucleic acid or HSD3B1 polypeptide sequence variant. Such articles of manufacture can include two or more sequence variants of HSD3B1, or can include all of the sequence variants known for HSD3B1. For example, the article of manufacture can include two or more of the sequence variants identified herein and one or more other HSD3B1 sequence variants, such as nucleic acid variants that occur in the promoter region of the HSD3B1 gene.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al. (1996) *Nature Genet.* 14:441-447; and U.S. Pat, Nos. 5,770, 722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 Caucasian-American, 60 African-American subjects, 60 Han Chinese American subjects, and 60 Mexican-American subjects (sample sets HD100CAU, HD100AA, HD100CHI, and CH100MEX) were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Three PCR reactions were performed with each DNA sample to amplify all HSD3B1 exons and splice junctions. The amplicons were then sequenced using dye-primer sequencing chemistry to facilitate the identification of heterozygous bases (Chadwick et al. (1996) *Biotechniques* 20:676-683). To make that possible, universal M13 sequencing tags were added to the 5'-ends of some of the forward and reverse primers. Particular forward primers (see Table 1) contained the M13 forward sequence (5'-TGTAAAACGACGGCCAGT-3'; SEQ ID NO:7), and certain reverse primers (see Table 1) contained the M13 reverse sequence (5'-CAGGAAACAGCTATGACC-3'; SEQ ID NO:8). The sequences and locations of each primer within the gene are listed in Table 1. "F" represents forward; "R," reverse; "U," upstream; "D," downstream; "I," intron; "FR," flanking region; and "UTR," untranslated region. The locations of primers within the gene were chosen to avoid repetitive sequence.

Amplifications were performed with AmpliTaq Gold DNA polymerase (Perkin Elmer, Foster City, Calif.) using a "hot start" to help ensure amplification specificity.

Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. To exclude PCR-induced artifacts, independent amplification followed by DNA sequencing was performed for all samples in which a SNP was only observed once among the samples resequenced. DNA sequence chromatograms were analyzed using the PolyPhred 3.0 (Nickerson et al. (1997) *Nucl. Acids Res.* 25:2745-2751) and Consed 8.0 (Gordon et al. (1998) *Genome Res.* 8:195-202) programs developed by the University of Washington (Seattle, Wash.). The University of Wisconsin GCG software package, Version 10, was also used to analyze nucleotide sequence. GenBank accession numbers for the HSD3B1 reference sequences were NT_004754 and NM_000862.

HSD3B1 expression constructs and COS-1 cell transfection: The wild type (WT) HSD3B1 sequence (GenBank accession number NM_000862) was amplified using human cDNA (e.g., human placenta cDNA; Clontech) as template and cloned into the eukaryotic expression vector pcDNA4/HisMax-TOPO® TA. The WT construct was then used as the template for site-directed mutagenesis, performed using circular PCR to create variant constructs. The Asn367Thr variant construct was used as a template to create the double variants Ser96Phe, Asn367Thr and Phe286Leu, Asn367Thr. The Ile79Val variant construct was used to create the Ile79Val, Phe286Leu double variant construct, which in turn was used to create the triple variant construct that also contained Asn367Thr. The primers used for site-directed mutagenesis are listed in Table 2. Sequences of the constructs were confirmed by sequencing both strands of the insert.

Expression constructs were transiently expressed in COS-1 cells using the TransFast reagent (Promega, Madison, Wis.) at a charge ratio of 1:1. Specifically, 10 µg of HSD3B1 expression construct DNA was cotransfected with 2 µg of pSV-β-Galactosidase DNA (Promega) to correct for transfection efficiency. After 48 hours, cells were lysed in 0.1% NP40 lysis buffer, followed by centrifugation at 3000 g for 10 minutes. Supernatants were used for Western blot analysis.

HSD3B1 reporter gene constructs and luciferase assay: Luciferase reporter gene constructs were created for the most common human HSD3B1 5'-FR haplotype (frequency ≧3% in any of the populations). Specifically, a segment containing about 1000 bp of the HSD3B1 5'-FR was amplified from human genomic DNA samples that contained the desired haplotypes. The forward and reverse primers included A CC651 and XhoI restriction sites, respectively, to enable subcloing of the amplicons into pGL-3 Basic (Promega), upstream of the firefly luciferase gene open reading frame (ORF). The forward and reverse primers for the amplifications of HSD3B1 5'-FR were GGTAACGGAAC-CCAGGGCTCTCCAGGGGCAAAT (SEQ ID NO:9) and CTCGAGGGCCATCCAAAGTAGCAGGGAT (SEQ ID NO:10), respectively. The insert was sequenced in both directions to ensure that the correct sequence was present.

The luciferase reporter gene constructs were designated as HSD3B1 pGL3WT and pGL3(-236T/C), and were used to transiently transfect MCF-7, DU-145, and JEG cell lines (ATCC, Manassas, Va.). All of these have been demonstrated to have HSD3B1 luciferase activity. Cells were transfected with 5 µg purified plasmid DNA with 50 ng pRL-TK (Promega) DNA. The Renilla luciferase activity expressed by pRL-TK was used as a control for transfection efficiency. Cells also were transfected with pGL-3 Basic without insert as a control. Transfection was performed using the TransFast reagent (Promega). After 48 hours, cells were lysed and reporter gene activity was measured using a Promega dual-luciferase assay system. Results are reported as the ratio of firefly luciferase light units to Renilla luciferase light units, and all values are expressed as a percentage of the activity of the pGL3 WT 5'-FR construct. All assays in three cell lines were performed in triplicate.

Western blot analysis: Supernatants of COS-1 cell lysates containing expressed WT and variant expression constructs were used for Western blot analysis. After correction for β-galactosidase activity, cell lysates were loaded on 12% SDS PAGE and then transferred onto PVDF membrane (Bio-Rad Laboratories, Hercules, Calif.), followed by blotting with a monoclonal anti-His antibody (Sigma, St Louis, Mo). Results were quantified using the AMBIS Radioanalytic Imaging System, Wuant ProbeVersion 4.31 (Ambis, Inc., San Diego, Calif.), and the data are expressed as a percentage of the intensity of the WT HSD3B1.

In vitro translation and degradation: Transcription and translation of HSD3B1 allozymes were performed using the TNT coupled RRL System (Promega). Specifically, 1 µg expression construct was added to 25 µL RRL that had been treated to inhibit protein degradation, together with 2 µL T7 buffer, 1 µL T7 polymerase, 1 µL of a mixture of amino acids that lacked methionine, 1 µL RNasin, and 2 µL $^{35}$S-methionine (1000 Ci/mM, 10 mCi/mL, 0.4 µM final concentration). With the exception of the RNasin (Promega) and $^{35}$S-methionine (Amersham Pharmacia Biotech), all reagents were included in the Promega kit. The reaction volume was increased to 50 µL with nuclease-free water (Promega), and the mixture was incubated at 30° C. for 90 minutes. A 5 µL aliquot was then used to perform SDS-PAGE, followed by autoradiography.

For protein degradation experiments, 10 µL of in vitro translated $^{35}$S-methionine-labeled protein were added to 50 µL of an adenosine 5'-triphosphate (ATP) generating system and 50 µL of "untreated" RRL. The ATP generating system contained 100 µL each of 1 M Tris-HCl (pH 7.8), 160 mM $MgCl_2$, 120 mM KCl, 100 mM dithiothreitol, 100 mM ATP, 200 mM creatine phosphate, and 2 mg/mL creatine kinase (all from Sigma), plus 300 µL nuclease-free water (Promega). This mixture was incubated at 37° C., and aliquots were removed at 0, 4, and 8 hours for SDS-PAGE followed by autoradiography. $^{35}$S-methionine radioactively-labeled protein was quantified using the AMBIS System.

Quantitative RT-PCR: mRNA was isolated from COS-1 cells that had been cotransfected with a control β-Galactosidase reporter and an HSD3B1 WT expression construct or an HSD3B1 variant 287 expression construct using an RNeasy Mini Kit (Qiagen, Valencia, Calif.), according to the manufacturer's instructions. RT-PCR was performed with primers for both HSD3B1 and β-Galactosidase as an internal control.

Confocal microscopy: Fluorescein isothiocyanate (FITC)-conjugated goat anti-mouse immunoglobulin and tetramethylrhodamine isothiocyanate (TRITC)-conjugated goat anti-rabbit immunoglobulin were purchased from Southern Biotech (Birmingham, Ala.). COS-1 cells were subcultured to 50-70% confluence on coverslips, transfected with expression constructs, and cultured for 48 hours. The cells were washed with phosphate buffered saline (PBS), fixed with 3% paraformaldehyde for 12 minutes at room temperature, washed, and incubated at room temperature for 5 minutes with buffer containing 0.5% Triton X-100. The coverslips were then incubated with primary antibodies—rabbit polyclonal antihuman antibody against calnexin (an endoplasmic reticulum marker) and mouse monoclonal anti-His antibody, followed by FITC-conjugated goat anti-mouse or TRITC-conjugated goat anti-rabbit IgG antibody. The COS-1 cells were viewed using a Zeiss LSM 510 confocal microscope with 488 or 570 nm filters for excitation of the green or red fluorochrome, respectively.

Data Analysis: Statistical comparison of the data was performed by ANOVA using the StatView program, version 4.5 (Abacus Concepts, Inc., Berkeley, Calif.). Linkage analysis was performed after all DNA samples had been genotyped at each of the polymorphic sites observed, using the EH program developed by Terwilliger and Ott, *Handbook of Human Genetic Linkage*, The Johns Hopkins University Press, Baltimore, pp. 188-193 (1994). D' values, a quantitative method for reporting linkage data that is independent of allele frequency (Hartl and Clark *Principles of Population Genetics, 3rd* edition, Sinauer Associates, Inc., (Sunderland, Mass.), pp. 96-106 (1997); and Hedrick *Genetics of Populations, 2nd* edition, Jones and Bartlett (Sudbury, Mass.), pp. 396-405 (2000)), were calculated. The genotype data also were used to assign inferred haplotypes using a program based on the E-M algorithm (Long et al. (1995) *Am. J Hum. Genet.* 56:799-810; and Excoffier and Slatkin (1995) *Mol. Biol. Evol.* 12:921-927). Unambiguous haplotype assignment was possible on the basis of genotype for samples that contained no more than one heterozygous polymorphism.

HSD3B1 Enzyme Activity: HSD3B1 dehydrogenase or isomerase activity is measured using the method described by Thomas et al. (supra). Briefly, an HSD3B1 preparation (e.g., a purified enzyme preparation) is incubated with a substrate such as DHEA, pregnenolone, or 17α-hydroxypregnenolone in the presence of NAD$^+$, and dehydrogenase activity is measured as absorbance at 340 nm due to NADH production. Alternatively, an HSD3B1 preparation is incubated with 5-androstene-3,17-dione in the presence of NADH, and isomerase activity is measured as absorbance at 241 nm due to androstenedione formation.

TABLE 1

PCR primers used for resequencing HSD3B1

| Forward/Reverse | Primer Name | Primer Location | Primer Sequence (5' to 3' direction) | SEQ ID NO |
|---|---|---|---|---|
| F | UF(-668) | Exons 1 and 2 | GGAACCCAGGGCTCTCCAGGGGCAAATGA | 11 |
| R | I2R(423) | Exons 1 and 2 | CACAGCCTGGCACGTTCTAGAGAGACAAT | 12 |
| F | UF(-648) | 5'FR | TGTAAAACGACGGCCAGTGGCAAATGACCATTGAGGTTTCA | 13 |
| R | E1R(-119) | 5'FR | CAGGAAACAGCTATGACCGTGGACGTAGTTCTCACCTCATTT | 14 |
| F | UF(-234) | Exons 1 and 2 | TGTAAAACGACGGCCAGTGGAGGAGAGAGCAATGAGTAGA | 15 |
| R | I2R(171) | Exons 1 and 2 | CAGGAAACAGCTATGACCCATACTATGCGATTTATACTATTTAATATTTA | 16 |
| F | I2F(-233) | Exon 3 | TGTAAAACGACGGCCAGTGATTACTTTTCTAAAATGAGATGGGAG | 17 |
| R | I3R(157) | Exon 3 | CAGGAAACAGCTATGACCGTTAGCAGTCTTGAACTCTGCTAT | 18 |
| F | I3F(-123) | Exon 4 | GTACCCTGAGTCTGTTACAACCACCAT | 19 |
| R | 3'UTR(1442) | Exon 4 | GTAGAAATGGAGCTCTAGTAGTCAAAACG | 20 |
| F | I3F(-82) | Exon 4 | TGTAAAACGACGGCCAGTGGTGGGGCACATAGATCTGTGTT | 21 |
| R | E4(768) | Exon 4 | CAGGAAACAGCTATGACCGATATAGTAGAACTGTCCTCGGATG | 22 |
| F | E4(661) | Exon 4 | TGTAAAACGACGGCCAGTGTTAACCCAGTCTATGTTGGCAAT | 23 |
| R | 3'UTR(1223) | Exon 4 | CAGGAAACAGCTATGACCCCTGAGCTTGTGCCCTTGTCACT | 24 |

Underlined nucleotides indicate M13 tag

TABLE 2

PCR primers used for mutagenesis

| Forward/Reverse | Mutation | Primer Sequence (5' to 3' direction) | SEQ ID NO |
|---|---|---|---|
| F | Ile79Val | GAGGACGTCTCGGTCGTCATCCACACCGCCT | 25 |
| R | Ile79Val | AGGCGGTGTGGATGACGACCGAGACGTCCTG | 26 |
| F | Ser96Phe | CACTCACAGAGAGTTTATGATGAATGTCA | 27 |
| R | Ser96Phe | TGACATTCATGATAAACTCTCTGTGAGTG | 28 |
| F | Asp242Asn | TGAGGGCCCTGCAGAACCCCAAGAAGGCCC | 29 |
| R | Asp242Asn | GGGCCTTGTTGGGGTTCTGCAGGGCCCTCA | 30 |
| F | Phe286Leu | GATTCCAGATGGAGCCTTCCTTTATCCCTGA | 31 |
| R | Phe286Leu | TCAGGGATAAAGGAAGGCTCCATCTGGAATC | 32 |

TABLE 2-continued

PCR primers used for mutagenesis

| Forward/Reverse | Mutation | Primer Sequence (5' to 3' direction) | SEQ ID NO |
|---|---|---|---|
| F | Asn367Thr | CCGGCACAAGGAGACCCTGAAGTCCAAG | 33 |
| R | Asn367Thr | CTTGGACTTCAGGGTCTCCTTGTGCCGG | 34 |

EXAMPLE 2

HSD3B1 Polymorphisms

Three separate PCR amplifications were performed for each of the DNA samples studied. All PCR amplicons were sequenced on both strands, making it possible to verify the presence of polymorphisms using data from the complimentary strand. A total of seventeen polymorphisms were observed (Table 3). Polymorphisms in exons and the 5' flanking region (FR) are numbered relative to the adenine in the HSD3B1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.0% to 60.8%, with differences between the African-American, Caucasian-American, Han Chinese-American, and Mexican-American subjects. Twelve polymorphisms were observed in 60 DNA samples from African-American subjects, while four were found in the 60 samples from Caucasian-American subjects, twelve were found in the 60 samples from Han Chinese-American subjects, and nine were found in the 60 samples from Mexican-American subjects. Twelve of the SNPs were within the coding-region (cSNPs), and five of those cSNPs—located in exons 3 and 4—were nonsynonymous and resulted in the amino acid alterations Ile79Val, Ser96Phe, Asp242Asn, Phe286Leu, and Asn367Thr. The Ile79Val polymorphism had a frequency of 33.1% African-Americans, 4.2% in Han Chinese-Americans, and 2.5% in Mexican-Americans, but was not observed in DNA from Caucasian-American subjects. The Ser96Phe polymorphism had a frequency of 0.9% in Caucasian-Americans, but was not observed in DNA from African-Americans, Han Chinese-Americans, or Mexican-Americans. The Asp242Asn polymorphism had a frequency of 1.7% in Han Chinese-Americans, but was not observed in African-Americans, Caucasian Americans, or Mexican Americans. The Phe286Leu polymorphism had a frequency of 35.8% in African-Americans, 0.8% in Caucasian-Americans, and 3.3% in both Han Chinese-Americans and Mexican-Americans. The Asn367Thr polymorphism had a frequency of 11.7% in African-Americans, 31.0% in Caucasian-Americans, 8.5% in Han Chinese-Americans, and 17.5% in Mexican-Americans. To exclude artifacts introduced by PCR-dependent misincorporation, independent amplifications were performed and the amplicons were sequenced in all cases in which a polymorphism was observed only once among the DNA samples studied.

TABLE 3

Human HSD3B1 polymorphisms and frequencies

| Polymorphism Position | Location In Gene | Position in SEQ ID 1 | Amino Acid Change | WT Sequence Nucleotide | Variant Sequence Nucleotide | AA | CA | HCA | MA |
|---|---|---|---|---|---|---|---|---|---|
| −515 | 5'-FR | 735 | | C | T | 0.000 | 0.000 | 0.008 | 0.000 |
| −365 | 5'-FR | 885 | | T | C | 0.308 | 0.000 | 0.042 | 0.033 |
| 48 | Intron 1 | 1083 | | C | A | 0.033 | 0.000 | 0.000 | 0.000 |
| 56 | Intron 2 | 1450 | | G | T | 0.175 | 0.000 | 0.042 | 0.025 |
| −22 | Intron 2 | 5254 | | G | C | 0.000 | 0.000 | 0.008 | 0.000 |
| 166 | Exon 3 | 5296 | | C | T | 0.026 | 0.000 | 0.000 | 0.000 |
| 228 | Exon 3 | 5358 | | C | T | 0.319 | 0.000 | 0.042 | 0.025 |
| 235 | Exon 3 | 5365 | Ile79Val | A | G | 0.331 | 0.000 | 0.042 | 0.033 |
| 270 | Exon 3 | 5400 | | T | A | 0.314 | 0.000 | 0.042 | 0.025 |
| 287 | Exon 3 | 5417 | Ser96Phe | C | T | 0.000 | 0.009 | 0.000 | 0.000 |
| 724 | Exon 4 | 8020 | Asp242Asn | G | A | 0.000 | 0.000 | 0.017 | 0.000 |
| 856 | Exon 4 | 8152 | Phe286Leu | T | C | 0.358 | 0.008 | 0.033 | 0.033 |
| 933 | Exon 4 | 8229 | | T | C | 0.000 | 0.000 | 0.008 | 0.000 |
| 939 | Exon 4 | 8235 | | G | A | 0.142 | 0.000 | 0.000 | 0.000 |
| 1012 | Exon 4 | 8308 | | C | T | 0.117 | 0.388 | 0.608 | 0.608 |
| 1017 | Exon 4 | 8313 | | G | A | 0.017 | 0.000 | 0.000 | 0.008 |
| 1100 | Exon 4 | 8395 | Asn367Thr | A | C | 0.117 | 0.310 | 0.085 | 0.175 |

AA, African Americans;
CA, Caucasian Americans;
HCA, Han Chinese Americans;
MA, Mexican Americans

EXAMPLE 3

Linkage Disequilibrium Analysis and Haplotype Analysis

Linkage disequilibrium analysis was performed after all of the DNA samples had been genotyped at each of the 17 polymorphic sites. Pairwise combinations of these polymorphisms were tested for linkage disequilibrium using the EH program developed by Terwilliger and Ott, *Handbook of Human Genetic Linkage*, The Johns Hopkins University Press, Baltimore, pp. 188-193 (1994). The output of this program was used to calculate d' values, a method for reporting linkage data that is independent of sample size. Pairwise combinations with a statistically significant linkage disequilibrium (P-value<0.001) are shown in Tables 4 and 5. D' values greater than 0 indicate a positive association, while d' values less than 0 indicate a negative association.

The genotype data also were used for haplotype analysis (Tables 6-9). Twenty-three unequivocal haplotypes were identified by these studies. Only haplotypes having frequencies greater than or equal to 0.8% are included in Tables 6-9. As shown in the tables, the haplotype analysis accounted for 99.8% of all DNA samples from Caucasian-American subjects, 99.6% of all DNA samples from African-American subjects, 97.9% of all DNA samples from Han Chinese-American subjects, and 100% of all DNA samples from Mexican-American subjects. The haplotypes included one that was ethnic-specific for Caucasian-American subjects, thirteen that were ethnic-specific for African-American subjects, two that were ethnic-specific for Han Chinese-American subjects, one that was ethnic-specific for Mexican-American subjects, two that were common to Caucasian-American and African-American subjects, one that was common to Han Chinese-American and Mexican-American subjects, one that was common to Caucasian-American, Han Chinese-American, and Mexican-American subjects, and two that were common to all four ethnic groups. Interestingly, haplotypes containing either Ile79Val or Ser96Phe alone typically were not observed. Instead, combinations of Ile79Val with Phe286Leu and Ser96Phe with Asn367Thr were more frequently observed.

TABLE 4

Linkage Disequilibrium Statistics

| Caucasian American Population | | | | African American Population | | | |
|---|---|---|---|---|---|---|---|
| Location 1 | Location 2 | D' Value | P-Value | Location 1 | Location 2 | D' Value | P-Value |
| Exon 4 (1012) | Exon 4 (1100) | −0.9123 | 1.00E−06 | 5'FR (−365) | Intron 2 (56) | 0.9194 | 0 |
| | | | | 5'FR (−365) | Exon 3 (228) | 0.9584 | 0 |
| | | | | 5'FR (−365) | Exon 3 (235) | 1 | 0 |
| | | | | 5'FR (−365) | Exon 3 (270) | 0.9588 | 0 |
| | | | | 5'FR (−365) | Exon 4 (856) | 0.955 | 0 |
| | | | | 5'FR (−365) | Exon 4 (939) | 0.8945 | 7.00E−06 |
| | | | | Intron 2 (56) | Exon 3 (228) | 1 | 0 |
| | | | | Intron 2 (56) | Exon 3 (235) | 1 | 0 |
| | | | | Intron 2 (56) | Exon 3 (270) | 1 | 0 |
| | | | | Intron 2 (56) | Exon 4 (856) | 1 | 0 |
| | | | | Exon 3 (228) | Exon 3 (235) | 1 | 0 |
| | | | | Exon 3 (228) | Exon 3 (270) | 1 | 0 |
| | | | | Exon 3 (228) | Exon 4 (856) | 0.9562 | 0 |
| | | | | Exon 3 (228) | Exon 4 (939) | 1 | 0 |
| | | | | Exon 3 (235) | Exon 3 (270) | 1 | 0 |
| | | | | Exon 3 (235) | Exon 4 (856) | 0.9587 | 0 |
| | | | | Exon 3 (235) | Exon (939) | 1 | 0 |
| | | | | Exon 3 (270) | Exon 4 (856) | 0.9556 | 0 |
| | | | | Exon 3 (270) | Exon 4 (939) | 1 | 0 |
| | | | | Exon 4 (856) | Exon 4 (939) | 1 | 1.00E−06 |

TABLE 5

Linkage Disequilibrium Statistics

| Han Chinese Population | | | | Mexican American Population | | | |
|---|---|---|---|---|---|---|---|
| Location 1 | Location 2 | D' Value | P-Value | Location 1 | Location 2 | D' Value | P-Value |
| 5'FR (−365) | Intron 2 (56) | 1 | 0 | 5'FR (−365) | Intron 2 (56) | 1 | 1.10E−05 |
| 5'FR (−365) | Exon 3 (228) | 1 | 0 | 5'FR (−365) | Exon 3 (228) | 1 | 1.10E−05 |
| 5'FR (−365) | Exon 3 (235) | 1 | 0 | 5'FR (−365) | Exon 3 (235) | 1 | 0 |
| 5'FR (−365) | Exon 3 (270) | 1 | 0 | 5'FR (−365) | Exon 3 (270) | 1 | 1.10E−05 |
| 5'FR (−365) | Exon 4 (856) | 1 | 0 | 5'FR (−365) | Exon 4 (856) | 1 | 0 |
| Intron 2 (56) | Exon 3 (228) | 1 | 0 | Intron 2 (56) | Exon 3 (228) | 1 | 1.00E−06 |
| Intron 2 (56) | Exon 3 (235) | 1 | 0 | Intron 2 (56) | Exon 3 (235) | 1 | 1.10E−05 |
| Intron 2 (56) | Exon 3 (270) | 1 | 0 | Intron 2 (56) | Exon 3 (270) | 1 | 1.00E−06 |
| Intron 2 (56) | Exon 4 (856) | 1 | 0 | Intron 2 (56) | Exon 4 (856) | 1 | 1.10E−05 |
| Exon 3 (228) | Exon 3 (235) | 1 | 0 | Exon 3 (228) | Exon 3 (235) | 1 | 1.10E−05 |
| Exon 3 (228) | Exon 3 (270) | 1 | 0 | Exon 3 (228) | Exon 3 (270) | 1 | 1.00E−06 |
| Exon 3 (228) | Exon 4 (856) | 1 | 0 | Exon 3 (228) | Exon 4 (856) | 1 | 1.10E−05 |
| Exon 3 (235) | Exon 3 (270) | 1 | 0 | Exon 3 (235) | Exon 3 (270) | 1 | 1.10E−05 |
| Exon 3 (235) | Exon 4 (856) | 1 | 0 | Exon 3 (235) | Exon 4 (856) | 1 | 0 |

TABLE 5-continued

Linkage Disequilibrium Statistics

| Han Chinese Population | | | | Mexican American Population | | | |
|---|---|---|---|---|---|---|---|
| Location 1 | Location 2 | D' Value | P-Value | Location 1 | Location 2 | D' Value | P-Value |
| Exon 3 (270) | Exon 4 (856) | 1 | 0 | Exon 3 (270) | Exon 4 (856) | 1 | 1.10E−05 |
| | | | | Exon 4 (1012) | Exon 4 (1100) | 1 | 0 |

TABLE 6

HSD3B1 Haplotypes for Caucasian American Population

| Freq. | O/I* | 5'FR −515 | 5'FR −365 | Intron 1 48 | Intron 2 56 | Intron 2 −22 | Exon 3 166 | Exon 3 228 | Exon 3 235 | Exon 3 270 | Exon 3 287 | Exon 4 724 | Exon 4 856 | Exon 4 933 | Exon 4 939 | Exon 4 1012 | Exon 4 1017 | Exon 4 1100 |
|---|---|---|---|---|---|---|---|---|---|---|---|---|---|---|---|---|---|---|
| 38% | o | C | T | C | G | G | C | C | A | T | C | G | T | T | G | T | G | A |
| 30% | o | C | T | C | G | G | C | C | A | T | C | G | T | T | G | C | G | C |
| 29% | o | C | T | C | G | G | C | C | A | T | C | G | T | T | G | C | G | A |
| 1% | o | C | T | C | G | G | C | C | A | T | C | G | T | T | G | T | G | C |
| 0.9% | o | C | T | C | G | G | C | C | A | T | C | G | C | T | G | C | G | A |
| 0.9% | i | C | T | C | G | G | C | C | A | T | T | G | T | T | G | C | G | C |

*o = observed; i = inferred

TABLE 7

HSD3B1 Haplotypes for African American Population

| Freq. | O/I* | 5'FR −515 | 5'FR −365 | Intron 1 48 | Intron 2 56 | Intron 2 −22 | Exon 3 166 | Exon 3 228 | Exon 3 235 | Exon 3 270 | Exon 3 287 | Exon 4 724 | Exon 4 856 | Exon 4 933 | Exon 4 939 | Exon 4 1012 | Exon 4 1017 | Exon 4 1100 |
|---|---|---|---|---|---|---|---|---|---|---|---|---|---|---|---|---|---|---|
| 41% | o | C | T | C | G | G | C | C | A | T | C | G | T | T | G | C | G | A |
| 15% | o | C | C | C | T | G | C | T | G | A | C | G | C | T | G | C | G | A |
| 11% | o | C | C | C | G | G | C | T | G | A | C | G | C | T | A | C | G | A |
| 11% | o | C | T | C | G | G | C | C | A | T | C | G | T | T | G | C | G | C |
| 10% | o | C | T | C | G | G | C | C | A | T | C | G | T | T | G | T | G | A |
| 1.7% | i | C | C | C | T | G | T | T | G | A | C | G | C | T | G | C | G | A |
| 0.9% | o | C | T | C | G | G | C | C | A | T | C | G | C | T | G | C | G | A |
| 0.9% | i | C | C | C | G | G | C | T | G | A | C | G | T | T | G | C | G | A |
| 0.9% | i | C | C | C | G | G | C | C | G | T | C | G | C | T | G | C | A | A |
| 0.9% | i | C | T | C | T | G | C | T | G | A | C | G | C | T | G | C | G | A |
| 0.9% | i | C | T | C | G | G | T | C | A | T | C | G | C | T | A | C | G | C |
| 0.9% | i | C | T | C | G | G | C | T | G | A | C | G | C | T | A | C | A | A |
| 0.9% | i | C | T | C | G | G | C | C | G | T | C | G | C | T | G | C | G | A |
| 0.9% | i | C | T | A | G | G | C | C | A | T | C | G | C | T | G | C | G | A |
| 0.9% | i | C | T | A | G | G | C | C | A | T | C | G | T | T | G | T | G | A |
| 0.9% | i | C | C | A | G | G | C | T | G | A | C | G | C | T | A | C | G | A |
| 0.9% | i | C | C | A | T | G | C | T | G | A | C | G | C | T | G | C | G | A |

*o = observed; i = inferred

TABLE 8

HSD3B1 Haplotypes for Han Chinese American Population

| Freq. | O/I* | 5'FR −515 | 5'FR −365 | Intron 1 48 | Intron 2 56 | Intron 2 −22 | Exon 3 166 | Exon 3 228 | Exon 3 235 | Exon 3 270 | Exon 3 287 | Exon 4 724 | Exon 4 856 | Exon 4 933 | Exon 4 939 | Exon 4 1012 | Exon 4 1017 | Exon 4 1100 |
|---|---|---|---|---|---|---|---|---|---|---|---|---|---|---|---|---|---|---|
| 59% | o | C | T | C | G | G | C | C | A | T | C | G | T | T | G | C | G | A |
| 24% | o | C | T | C | G | G | C | C | A | T | C | G | T | T | G | T | G | A |
| 8.5% | o | C | T | C | G | G | C | C | A | T | C | G | T | T | G | T | G | C |
| 4.2% | i | C | C | C | T | G | C | T | G | A | C | G | C | T | G | T | G | A |
| 1.4% | o | C | T | C | G | G | C | C | A | T | C | A | T | T | G | C | G | A |
| 0.8% | o | T | T | C | G | G | C | C | A | T | C | G | T | T | G | C | G | A |

*o = observed; i = inferred

TABLE 9

HSD3B1 Haplotypes for Mexican American Population

| Freq. | O/I* | 5'FR −515 | 5'FR −365 | Intron 1 48 | Intron 2 56 | Intron 2 −22 | Exon 3 166 | Exon 3 228 | Exon 3 235 | Exon 3 270 | Exon 3 287 | Exon 4 724 | Exon 4 856 | Exon 4 933 | Exon 4 939 | Exon 4 1012 | Exon 4 1017 | Exon 4 1100 |
|---|---|---|---|---|---|---|---|---|---|---|---|---|---|---|---|---|---|---|
| 61% | o | C | T | C | G | G | C | C | A | T | C | G | T | T | G | C | G | A |
| 19% | o | C | T | C | G | G | C | C | A | T | C | G | T | T | G | T | G | A |
| 17% | o | C | T | C | G | G | C | C | A | T | C | G | T | T | G | T | G | C |
| 2.5% | i | C | C | C | T | G | C | T | G | A | C | G | C | T | G | T | G | A |
| 0.8% | i | C | C | C | G | G | C | C | G | T | C | G | C | T | G | T | A | C |

*o = observed; i = inferred

EXAMPLE 4

Immunoreactivity of HSD3B1 Allozymes

To determine the functional effects of the common non-synonymous cSNPs, expression constructs were prepared for WT HSD3B1 as well as allozymes including Ile79Val, Ser96Phe, Asp242Asn, Phe286Leu, and Asn367Thr. Several double and triple variants also were prepared, based on the haplotype analysis. These were Ile79Val, Phe286Leu; Ser96Phe, Asn367Thr; Phe286Leu, Asn367Thr; and Ile79Val, Phe286Leu, Asn367Thr. The constructs were transiently expressed in COS-1 cells. Cell homogenates containing recombinant allozymes were prepared and quantitative Western blot analysis was performed, correcting for β-Galactosidase activity. Results are shown in FIG. 3. Ser96Phe protein levels were decreased by more than 50% as compared with WT (p<0.001), while Asp242Asn protein levels showed about a 30% decrease (p<0.05).

EXAMPLE 5

In vitro Degradation of HSD3B1 Allozymes

To determine whether the effect of nonsynonymous HSD3B1 cSNPs on protein levels was due to accelerated degradation, in vitro degradation studies were performed for the Ser96Phe and Phe286Leu allozymes. In vitro-translated $^{35}$S-methionine-labeled HSD3B1 WT and Ser96Phe were mixed with an ATP generating system. Degradation assays were performed at 37° C. for 2, 4 and 8 hours, followed by analysis using SDS-PAGE. These experiments revealed that there was no significant difference in the rate of degradation between HSD3B1 WT and the variant Ser96Phe allozyme.

EXAMPLE 6 mRNA Levels of HSD3B1 Allozymes

RT-PCR was used to determine whether differences in protein levels were due to differences in mRNA levels. To evaluate the mRNA level after transient expression of HSD3B1 WT and the Ser96Phe allozyme, RT-PCR was performed using mRNA isolated from transfected COS-1 cells. β-Galactosidase was used to correct for transfection efficiency and also as an internal control for RT-PCR. These studies showed that mRNA levels for the allozymes were not significantly different from that of the WT HSD3B1 after the correction for the internal control.

EXAMPLE 7

Reporter Assays

Figure 4:
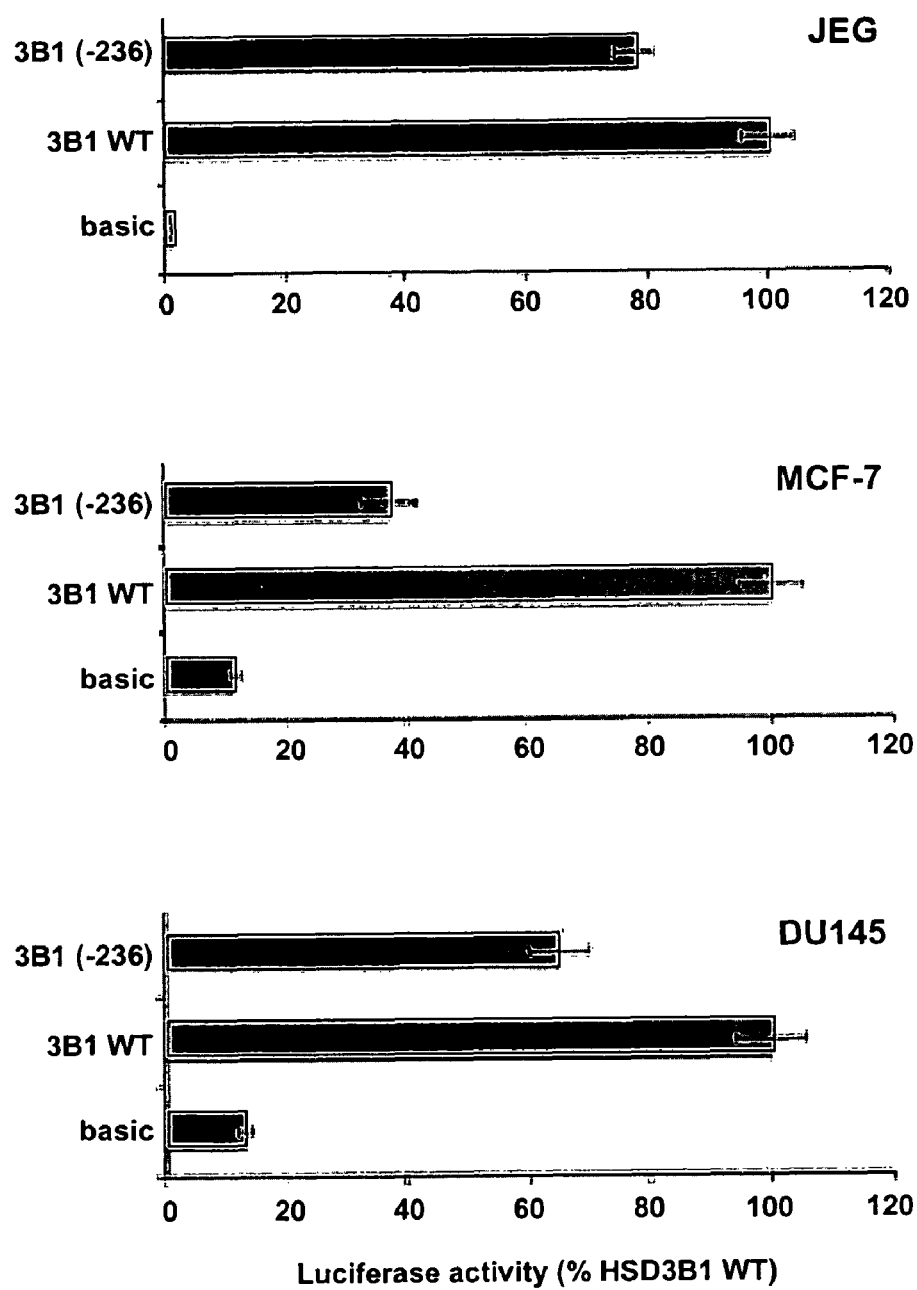
FIG. 4 is a series of graphs plotting luciferase activity from expression of the indicated reporter constructs in JEG cells (top panel), MCF-7 cells (middle panel), and DU145 cells (bottom panel).

Luciferase reporter assays were conducted to determine whether polymorphisms in the 5'-FR affected transcription of HSD3B1 allozymes. Reporter gene constructs including haplotypes with an allele frequency more than 3% were created within the first 1 kb upstream of the translation initiation codon. These constructs were transfected into breast cancer cell line MCF-7, prostate cancer cell line DU-145, and placental cell line JEG. Luciferase activity measured in these cells showed a very similar pattern, except that the overall activity was much higher in JEG cells than in the other two cell lines (FIG. 4). This is consistent with the fact that HSD3B1 is a major isoform expressed in placental tissue. The nucleotide change at −236 from C to T significantly decreased luciferase activity in all three cell lines (P<0.01 in all three lines).

EXAMPLE 8

Activity and Substrate Kinetics of HSD3B1 Allozymes

Cell homogenate preparations containing recombinant HSD3B1 allozymes, prepared as described in Example 1, are used to assess catalytic activity. The resulting activities are adjusted to a percentage of the WT HSD3B1 enzyme activity. Alterations in amino acid sequence can alter enzyme substrate affinity and/or catalytic efficiency. Substrate kinetic studies are conducted to determine whether the Ile79Val, Ser96Phe, Asp242Asn, Phe286Leu, and Asn367Thr allozymes differ from the WT HSD3B1 protein in these aspects.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A vector comprising an isolated nucleic acid molecule consisting essentially of:
   a) a sequence of ten to 100 contiguous nucleotides as set forth in SEQ ID NO:5, wherein the nucleotides are in the order shown in SEQ ID NO:5, and wherein said sequence includes nucleotide 166, 287, 724, 933, 939, or 1017 of SEQ ID NO:5, with the proviso that the nucleotide at position 166 is thymine, the nucleotide at position 287 is thymine, the nucleotide at osition 724 is adenine, the nucleotide at position 933 is cytosine, the nucleotide at position 939 is adenine, or the nucleotide at position 1017 is adenine;
   b) a sequence of ten to 100 contiguous nucleotides as set forth in SEQ ID NO:1, wherein the nucleotides are in the order shown in SEQ ID NO:1, and wherein said sequence includes nucleotide 735, 1083, or 5254 of SEQ ID NO:1, with the proviso that the nucleotide at position 735 is thymine, the nucleotide at position 1083 is adenine, or the nucleotide at position 5254 is cytosine; or
   c) a sequence fully complementary to a) or b).

2. The vector of claim 1, wherein said nucleic acid molecule is from 20 to 50 nucleotides in length.

3. An isolated nucleic acid encoding a polypeptide comprising the amino acid sequence set forth in SEQ ID NO:6, with the proviso that the amino acid sequence of said polypeptide comprises an amino acid sequence variant at residue 96 or residue 242 relative to the amino acid sequence of SEQ ID NO:6.

4. The isolated nucleic acid of claim 3, wherein said amino acid sequence variant is a phenylalanine at residue 96 or an asparagine at residue 242.

5. An isolated HSD3B1 polypeptide, wherein said polypeptide comprises the amino acid sequence set forth in SEQ ID NO:6, with the proviso that said polypeptide comprises an amino acid sequence variant at residue 96 or residue 246 relative to the amino acid sequence set forth in SEQ ID NO:6.

6. The isolated polypeptide of claim 5, wherein said amino acid sequence variant is a phenylalanine at residue 96 or an asparagine at residue 242.

* * * * *

SEQUENCE LISTING

<160> NUMBER OF SEQ ID NOS: 34

<210> SEQ ID NO 1
<211> LENGTH: 9824
<212> TYPE: DNA
<213> ORGANISM: Homo sapien

<400> SEQUENCE: 1

| | | | | | |
|---|---|---|---|---|---|
| ttgcctatga | ggtagattgg | gggaaggtca | gggaattaac | agggaacagg | cagaaaacaa | 60 |
| ctttctggag | tgacggaaat | ggtctatatc | ttttttgggg | tgctacttac | atgggcatat | 120 |
| ataactgtca | agttccactg | aactgaacac | tgaagacctg | gcatttttaa | tgcatgtaaa | 180 |
| ttatatttca | attttttga | gtaaagtgtc | ttgggaagct | tatggcggtg | atatttgggc | 240 |
| agttctgggg | cataggcttc | agaagcattc | acagtatgtc | cagttcaaga | atttgctgag | 300 |
| aatcgttttg | cagccaaaaa | tatggataag | ttcgaacacc | tatgataaga | gtcattgggg | 360 |
| catacaacca | caaatcccca | ctcttgtgat | acaggccata | tcattaagtg | gttatcacca | 420 |
| gatagctttc | cttcaatgat | gttgttcatc | taggaaccca | gggctctcca | ggggcaaatg | 480 |
| accattgagg | tttcagatat | attgggtagg | aaagaaagtc | acctcacata | aaactaagtg | 540 |
| attggagctg | tcaccattgc | aaatttctaa | attttgtaag | acagcagcaa | catttcaaat | 600 |
| gatagtctga | gagaggagat | aatgggctta | catggatttc | cctccagatg | gatttactga | 660 |
| acaagggcac | aattcaaatt | gcacttgcag | atttctcctg | gtctagttta | agttcacaga | 720 |
| ttgtggatcc | cagacagctg | gtatcaactg | actagtgtcc | tgttaaggct | aaacccaaga | 780 |
| ctctttgcca | cactgcagca | ttaggatggg | acttctcttc | ctgttcctgg | gaagaattag | 840 |
| agatgtaacc | caaaggtcac | tatttttctg | agataaggat | cccataggag | gagagagcaa | 900 |
| tgagtacatg | gccagagatc | aaagtgataa | gggttgggcc | agaagccaca | gtgcataaag | 960 |
| cttcagactt | gccacaggaa | atgaggtgag | aagtacgtcc | actcttctgt | ccagctttta | 1020 |
| acaatctaac | taatggttag | agattttca | ttttctttca | gctactcctg | cagtggtggg | 1080 |
| gacacagaat | gtttgcaaaa | aaatgggt | ggaggaaaat | gaggcatctg | tgtgagtata | 1140 |
| taaccatttg | acatctcttt | ttagccctct | ccagggtcac | cctagaatca | gatctgctcc | 1200 |
| ccagcatctt | ctgttttcctg | gtgagtgatt | cctgctactt | tggatggcca | tgacgggctg | 1260 |
| gagctgcctt | gtgacaggag | caggaggggtt | tctgggacag | aggatcatcc | gcctcttggt | 1320 |
| gaaggagaag | gagctgaagg | agatcagggt | cttggacaag | gccttcggac | cagaattgag | 1380 |
| agaggaattt | tctagtaagt | aaacttgggt | catgggtgtg | tggttccatc | ttaaacactg | 1440 |
| catgtatgtg | gggggagatg | gaccttgtct | agcaagttat | tgaaatttgt | agccaaatct | 1500 |
| aagccaatct | cacatccaaa | gtcatcaaga | ataaatatt | aaatagtata | aaatggcata | 1560 |
| gtatgaaaga | tactgggtgg | gatttccaga | gactagattc | tggccctgac | ccagaacttg | 1620 |
| agaagcagcc | acctcagcct | ccaggcctct | tttcttctca | tctagaaaat | cccacatcag | 1680 |
| ttctttgtct | tgtctgcaac | tcttttatgt | tctgaagctt | ttgtcttggc | aattgctgta | 1740 |
| caacattcat | aaaggacact | attaccctgg | agacctcacc | aatgggtcat | tgtctctcta | 1800 |
| gaacgtgcca | ggctgtgttt | tgttttgcag | cttccttagt | atcctttgtg | agggcaaaat | 1860 |
| aaaaggaagt | taaggtaaag | atgagtgtat | aagtgggtgt | gtgtgacaga | gagagaggaa | 1920 |
| aacaataagg | gggagagaga | gtcggggaga | gagtcggg | gagagagact | cagagagaga | 1980 |
| gacaatgaga | aagacagaga | aataatgaaa | aatatatagt | gagagagaga | gcatcagtga | 2040 |

```
gagaatgtgt gtgcacagtg cacagcacag agcagagaca gagtaagagg cagtataagg   2100
ccagacatgc ctcatttaga ttttgcatat atggcttttt tttaaaaaaa aaaaaacaaa   2160
acatttacct ctgttgctca tcatcaaaaa gaaattgact gcagaatttt ctgtggcaac   2220
tccttgtaca aatggcccca agaggcaggt agaaaaggca tcacatccaa caggacaatg   2280
aacgcatcaa ggtccggaat cacaaagcaa catgctaagg ccatctgatt gatgcgtagc   2340
agagctcaga ccagagcttt atccataggc tatttcacct ggccccagag ctgatgcttg   2400
gcaaagtgga tcttcagtct ctccctttgc tccttggtgt gccccaaaac aattccctgt   2460
cctcctcccc aacccagggg atttggggga ctgtgtgtct acatgtgggc tctggctgcc   2520
cagagggtcc tgccctgccc acagagaatc ccccacttga cagcactcag ggaccacacc   2580
caacactcta cttttgctct tctctgacct cttgaaatgt tcgatttctt ccaccctctg   2640
ttttaatgtt gtctttgata acaaatatg aaatgcttat aatccttgcc tgtgtctcag   2700
caatatttgc aatttaacat ctgaagccag aaaaaagcaa tgctcagcct agaggtattg   2760
ttcccctatg gtaaaaatgc agatcatata atagacaggc agggatctgt atgaagataa   2820
aaacagagaa agcattcagt gttctttttg tgccaggcac ttggccaaag gtttgccaac   2880
tcatttgctc ctcataacaa ccctatgaga tcggtaatat tatcctcctt ttttaaagat   2940
gaggagatag aaacagagag gttagttaac tttttgaagg tcccacagtt agcatatggc   3000
aaagctagat ttgaacccag acagactagt gcagcatctg tgctcttaag cagtagtttg   3060
tcttacagct ccctttaggcc ttcctctagc ccaacttaca ccataaaagc aactccattt   3120
agtctacata aaacacttgc caagtctaca gtgccttgga gaagaaggga gccatgactt   3180
catcaacaaa gtaccttttc ctagtccctc tagatccctg ggaactcact ggggaagagt   3240 cctttctct cagctttgga cttcttccac tttgacactc ctttgagcca gtctgtctga   3300
agtggcagca aagaagaagc agaggaaggc agcaggaagg gcagaggtgg aactagaacc   3360
agagaacatc ccactctcag gctgttaccc acatcaccac cagcagcctc ttccctgact   3420
cccccactcc aggaccttct tggagttgcc tgacaacggg aagaggttgg gagtagacaa   3480
aacatggcag aggcatcagg agagcaagtg gtcctgcttg taccccagga aggaatttct   3540
ccagcttcga attttttcact ctgaattttg ctctcactgg tctttggtct ttgttgccaa   3600
tttcagttaa actggcttat tctttggaaa agaatgatat taaacaacag aaaagttgat   3660
attaaacagc cagtcctgca cctggtgtac agggtacaag cttggaggca gggtgggcgt   3720
gtttaagcct tcactagaaa cgtgaccttta gatctgtccc ttaacctctc tgagactcag   3780
tttcctcact gataaagtgg gactcagaat acctacctca tgagatagct gtaaaaagaa   3840
ataaatatcc tgtaagttgc atacagatga taaagcacaa acaagtgtag agtatttatc   3900
caagctccat gtagcatggt gttcattttg tgggctaatt ccaggtgaca accttactgg   3960
cagcgtcact tcctgtggat ttcagaggaa cctgaagaca ttgatgttgt aaccactgcc   4020
tccagctaga cagctgcgat gttagttcat tggtggttaa ctcattttca gcattgctac   4080 ctgctttga tgatatctga taatagtttt ccagggaaat tcatcattga agcccaccca   4140
caattcctga gtaatgactc cactctcctc ccagttgccc aagcaggaaa ctgtaggggt   4200 gatttttatct tctcctttttc ctatcagctc agatccaata ggtaccagga ccttcaaggt   4260
aaggtctgaa attcaaacct ggtatatctc tcccctcctc tgcttccact gctggaccct   4320
gcttccagtc ctcatcgaaa ctttggcaca gacattctga ttaatcactt gatcatcagt   4380
```

```
ctttctcaaa tcccctatac cagtccattt tatatcctca agccaagatt aacttcctac    4440
accacaaccc tgcttttgtt ccttttttg ttgttgcttg tgtggttttc tttttttttt    4500
tttttttttt tttttttttt tttttttgag acaaggtggt cttgctctac cacccaggct    4560
agagtgcaga ggtgtgatct tggctcactg ccaggaacca gagaccccag cctccattta    4620
tcctcccacc tcagtctgca gagtagctgg gactgcaggc aggcacatgc caccatgccc    4680
agctatttca tgtattttaa tagaaatggg atttccccat gttgtccaag ctggtctcaa    4740
cctcctgcgc tccagtgatc catccatcac agcctcccaa agtgctggaa taacaggcat    4800
gagccacggg gcttggcctt tttgtcattt tattccaaat ataaataagg ggttttcttt    4860
aacatgatgc tggagtccca aaattatgat tctatacatg atttctcatt acttacagaa    4920
ttaacttcaa acttttccct catactctct acaatcacac tactctcctt agaaaatttg    4980
atgggcttcc catgactcta gcaatgctta tattccaggc atacctgaca gctcactgct    5040
cagattactt ttctaaaatg agatgggaga gaaacagatg tttgctcttt ccaagaaatt    5100
gatacacatg ctgatttctg tgcctttttt acttgttctt tccgtagaat gtacaccctc    5160
cactctaaca ccctactcta accatccttg aacacctatg taacatcacc tttatcagaa    5220
aacttctcag ccagatacag aaatcattcc aatgacctga cctgtgttca cacagaactc    5280
cagaacaaga ccaagctgac agtgctggaa ggagacattc tggatgagcc attcctgaag    5340
agagcctgcc aggacgtctc ggtcatcatc cacaccgcct gtatcattga tgtcttcggt    5400
gtcactcaca gagagtctat catgaatgtc aatgtgaaag gtatggtagg ctggggagga    5460
gatgcagcaa ggtggggaat taaggatcac aaagaagggc aggaagggaa gagaagtccc    5520
tccactgaac acctgctgtg ctctgggcca agtgcctttg ctgatcacta cgaataggag    5580
agttcaagac tgctaacttt agttttttag atgataaaac taggactgag agagggcaag    5640
taacttgtcc aaggtccccc aggtaagtaa gcaggtagga gagttagact ttaaactcat    5700
ccctgtgtga ctccaaaggc tctttctact gtgactccaa aagctctttc tactgtggtt    5760
ccaatcaaaa gtcaactaat ttctgacttc agactcttga tacccagaca cccccttgcct   5820
```

```
cagctcaggg gaggctgcaa ggtcctccca ctgcaggtgt taccagcaga ggacacactt    6840
ctctccccag ccctccacca ggctccacag gaaatgccag ggcagggttt aaaagaaggt    6900
ttatcacctc cactttacat aaccaggtaa acagagtcac agccagaatt ggaagcagct    6960
ttcccaggga atgcacaatc aggaagagtg tgggtttcca gcatctcccc acaacccact    7020
gcttgctcag tgactccagg atggtccttg tgacaaagtt ttattagagc ccagcaaaat    7080
gagaaaagta ccaacaattt catatatatt gaagagttta tattgcctat atacaatggt    7140
gtatgtgtgt gtgtgatgtg aattcttcaa ctgcccattt tgcctaagga ctggaactgt    7200
ccatattcac agagtatagc ctcctgattt tttagatttt aaatgatctg actttaatgg    7260
tactgattac aaatcataat ttgtcaatac ccttacttgg caaaataaaa agtgataacc    7320
ctaggtccct ttccaaaatt aaagtacaca cacacacaca tccatgaaac ccaaaagtct    7380
agaaattctt actctccaga acccacatgt cagtttctct tcattttggt attttttctta   7440 tggctgtagt acgaccaaat ctcagacaga accacagaag aatgtaccct gagtctgtta    7500
caaccaccat atttgggagt gggggtgggg gcacatagat ctgtgttcgt ggttggcacc    7560
tcttagggat atatcctgac agtgacaata tgctcttcat ggacaggtac ccagctcctg    7620
ttagaggcct gtgtccaagc tagtgtgcca gtcttcatct acaccagtag catagaggta    7680
gccgggccca actcctacaa ggaaatcatc cagaatggcc atgaagaaga gcctctggaa    7740
aacacatggc ccgctccata cccacacagc aaaaagcttg ctgagaaggc tgtactggcg    7800
gctaacgggt ggaatctgaa aaacggcggc accctgtaca cttgtgcctt acgacccatg    7860
tatatctatg gggaaggaag ccgattcctt tctgctagta taaacgaggc cctgaacaac    7920
aatgggatcc tgtcaagtgt tggaaagttc tccactgtta acccagtcta tgttggcaat    7980
gtggcctggg cccacattct ggccttgagg gccctgcagg accccaagaa ggccccaagc    8040
atccgaggac agttctacta tatctcagat gacacgcctc accaaagcta tgataacctt    8100
aattcacccc tgagcaaaga gttcggcctc cgccttgatt ccagatggag ctttccttta   8160
tccctgatgt attggattgg cttcctgctg gaaatagtga gcttcctact caggccaatt    8220
tacacctatc gaccgcccct caaccgccac atagtcacat tgtcaaatag cgtattcacc    8280
ttctcttata agaaggctca gcgagatctg gcgtataagc cactctacag ctgggaggaa    8340
gccaagcaga aaacggtgga gtgggttggt tcccttgtgg accggcacaa ggagaccctg    8400
aagtccaaga ctcagtgatt taaggatgac agagatgtgc atgtgggtat tgttaggaga    8460
tgtcatcaag ctccacccctc ctggcctcat acagaaagtg acaagggcac aagctcaggt    8520
cctgctgcct cccttttcata caatggccaa cttattgtat tcctcatgtc atcaaaacct    8580
gcgcagtcat tggcccaaca agaaggtttc tgtcctaatc atataccaga ggaaagacca    8640
tgtggtttgc tgttaccaaa tctcagtagc tgattctgaa caatttaggg actcttttaa    8700
cttgagggtc gttttgacta ctagagctcc atttctactc ttaaatgaga aaggatttcc    8760
tttcttttta atcttccatt ccttcacata gtttgataaa aagatcaata aatgtttgaa    8820
tgtttaatgt ggagggaggt gtgagttatg ttaatacata ctttcctcct ttctccttct    8880
tttccaggta ttgccatctc caatttagaa gagtagcata aaacctgggt tggggagagg    8940
gcagagtagt gggagggcca ggaagggcgg atgaagactg aataagctct actaccttc     9000 aggcatgtac aacatgacct acatatgaca tatattatct tatttaatac tcatcagaaa    9060
cctatctggt gggggtgact aatcccattt taccactgag gaaacttgtt cacagtcaca    9120
```

-continued

```
ctaactgatt agtggctatg cctgctacca gggagttggc cttgaaagtc cttatctttc    9180
cacggaatca cgcagcctga actggtcttg tcagtggtac agcagagcac tggagcatgc    9240
agtgccgata cgtggaagag acccatctcc gttgggttac ctccttcttg cccagtccca    9300
tgcaggggac tctctagaac ccaggagaat ccctggggag catctggaag ggtttgaatg    9360
ccttaacaaa tggccctgag caggggtgag tgaagcaaaa atgcctccag cctccacctt    9420
caatgccaat ttccttgaag gtctctagaa cacacctggc tatatgtgtg ttagtcattc    9480
tgatcataca taaccctgca tttcacccct tcaaatcaca cagtgaagcc acaccatggg    9540
ttcctgggca agtaaaggga acaagtttaa acttccccca aaatgtgcct tctattcagc    9600
ccaagaagta agtctactgt cccacatccc cagatttaac tgcctctctc ttcattctcc    9660
ttctcttctt gagatcatat cttttcctcc tttattcttt catctcctta gcctctttcc    9720
ttccctccaa atcccttaa atcactggct ctctcattct tctcaatttc cctgaggaaa    9780
ggaggctaat caagacaagc ttggggactt cgatgatgac atag                    9824
```

<210> SEQ ID NO 2
<211> LENGTH: 48
<212> TYPE: PRT
<213> ORGANISM: Homo sapien

<400> SEQUENCE: 2

Met Thr Gly Trp Ser Cys Leu Val Thr Gly Ala Gly Phe Leu Gly
1               5                   10                  15

Gln Arg Ile Ile Arg Leu Leu Val Lys Glu Lys Glu Leu Lys Glu Ile
            20                  25                  30

Arg Val Leu Asp Lys Ala Phe Gly Pro Glu Leu Arg Glu Glu Phe Ser
        35                  40                  45

<210> SEQ ID NO 3
<211> LENGTH: 55
<212> TYPE: PRT
<213> ORGANISM: Homo sapien

<400> SEQUENCE: 3

Lys Leu Gln Asn Lys Thr Lys Leu Thr Val Leu Glu Gly Asp Ile Leu
1               5                   10                  15

Asp Glu Pro Phe Leu Lys Arg Ala Cys Gln Asp Val Ser Val Ile Ile
            20                  25                  30

His Thr Ala Cys Ile Ile Asp Val Phe Gly Val Thr His Arg Glu Ser
        35                  40                  45

Ile Met Asn Val Asn Val Lys
    50                  55

<210> SEQ ID NO 4
<211> LENGTH: 270
<212> TYPE: PRT
<213> ORGANISM: Homo sapien

<400> SEQUENCE: 4

Gly Thr Gln Leu Leu Leu Glu Ala Cys Val Gln Ala Ser Val Pro Val
1               5                   10                  15

Phe Ile Tyr Thr Ser Ser Ile Glu Val Ala Gly Pro Asn Ser Tyr Lys
            20                  25                  30

Glu Ile Ile Gln Asn Gly His Glu Glu Glu Pro Leu Glu Asn Thr Trp
        35                  40                  45

Pro Ala Pro Tyr Pro His Ser Lys Lys Leu Ala Glu Lys Ala Val Leu

```
                50                  55                  60
Ala Ala Asn Gly Trp Asn Leu Lys Asn Gly Gly Thr Leu Tyr Thr Cys
 65                  70                  75                  80

Ala Leu Arg Pro Met Tyr Ile Tyr Gly Glu Gly Ser Arg Phe Leu Ser
                 85                  90                  95

Ala Ser Ile Asn Glu Ala Leu Asn Asn Asn Gly Ile Leu Ser Ser Val
            100                 105                 110

Gly Lys Phe Ser Thr Val Asn Pro Val Tyr Val Gly Asn Val Ala Trp
        115                 120                 125

Ala His Ile Leu Ala Leu Arg Ala Leu Gln Asp Pro Lys Lys Ala Pro
    130                 135                 140

Ser Ile Arg Gly Gln Phe Tyr Tyr Ile Ser Asp Asp Thr Pro His Gln
145                 150                 155                 160

Ser Tyr Asp Asn Leu Asn Tyr Thr Leu Ser Lys Glu Phe Gly Leu Arg
                165                 170                 175

Leu Asp Ser Arg Trp Ser Phe Pro Leu Ser Leu Met Tyr Trp Ile Gly
            180                 185                 190

Phe Leu Leu Glu Ile Val Ser Phe Leu Leu Arg Pro Ile Tyr Thr Tyr
        195                 200                 205

Arg Pro Pro Phe Asn Arg His Ile Val Thr Leu Ser Asn Ser Val Phe
    210                 215                 220

Thr Phe Ser Tyr Lys Lys Ala Gln Arg Asp Leu Ala Tyr Lys Pro Leu
225                 230                 235                 240

Tyr Ser Trp Glu Glu Ala Lys Gln Lys Thr Val Glu Trp Val Gly Ser
                245                 250                 255

Leu Val Asp Arg His Lys Glu Thr Leu Lys Ser Lys Thr Gln
            260                 265                 270

<210> SEQ ID NO 5
<211> LENGTH: 1122
<212> TYPE: DNA
<213> ORGANISM: Homo sapien

<400> SEQUENCE: 5
atgacgggct ggagctgcct tgtgacagga gcaggagggt ttctgggaca gaggatcatc      60
cgcctcttgg tgaaggagaa ggagctgaag gagatcaggg tcttgacaa ggccttcgga     120
ccagaattga gagggaatt ttctaaactc cagaacaaga ccaagctgac agtgctggaa     180
ggagacattc tggatgagcc attcctgaag agagcctgcc aggacgtctc ggtcatcatc     240
cacaccgcct gtatcattga tgtcttcggt gtcactcaca gagagtctat catgaatgtc     300
aatgtgaaag gtacccagct cctgttagag gcctgtgtcc aagctagtgt gccagtcttc     360
atctacacca gtagcataga ggtagccggg cccaactcct acaaggaaat catccagaat     420
ggccatgaag aagagcctct ggaaaacaca tggcccgctc catacccaca cagcaaaaag     480
cttgctgaga aggctgtact ggcggctaac gggtggaatc tgaaaaacgg cggcaccctg     540
tacacttgtg ccttcgacc catgtatatc tatggggaag aagccgatt cctttctgct     600
agtataaacg aggccctgaa caacaatggg atcctgtcaa gtgttggaaa gttctccact     660
gttaacccag tctatgttgg caatgtggcc tgggcccaca ttctggcctt gagggccctg     720
caggacccca agaaggcccc aagcatccga ggacagttct actatatctc agatgacacg     780
cctcaccaaa gctatgataa ccttaattac accctgagca agagttcgg cctccgcctt     840
gattccagat ggagctttcc tttatccctg atgtattgga ttggcttcct gctggaaata     900
```

```
gtgagcttcc tactcaggcc aatttacacc tatcgaccgc ccttcaaccg ccacatagtc    960
acattgtcaa atagcgtatt caccttctct tataagaagg ctcagcgaga tctggcgtat   1020
aagccactct acagctggga ggaagccaag cagaaaacgg tggagtgggt tggttccctt   1080
gtggaccggc acaaggagac cctgaagtcc aagactcagt ga                      1122
```

<210> SEQ ID NO 6
<211> LENGTH: 355
<212> TYPE: PRT
<213> ORGANISM: Homo sapien

<400> SEQUENCE: 6

```
Met Thr Gly Trp Ser Cys Leu Val Thr Gly Ala Gly Phe Leu Gly
 1               5                  10                  15

Gln Arg Ile Ile Arg Leu Leu Val Lys Glu Lys Glu Leu Lys Glu Ile
                20                  25                  30

Arg Val Leu Asp Lys Ala Phe Gly Pro Glu Leu Arg Glu Glu Phe Ser
            35                  40                  45

Lys Leu Gln Asn Lys Thr Lys Leu Thr Val Leu Glu Gly Asp Ile Leu
        50                  55                  60

Asp Glu Pro Phe Leu Lys Arg Ala Cys Gln Asp Val Ser Val Ile Ile
65                  70                  75                  80

His Thr Ala Cys Ile Ile Asp Val Phe Gly Val Thr His Arg Glu Ser
                85                  90                  95

Ile Met Asn Val Asn Val Lys Gly Thr Gln Leu Leu Leu Glu Ala Cys
            100                 105                 110

Val Gln Ala Ser Val Pro Val Phe Ile Tyr Thr Ser Ser Ile Glu Val
        115                 120                 125

Ala Gly Pro Asn Ser Tyr Lys Glu Ile Ile Gln Asn Gly His Glu Glu
    130                 135                 140

Glu Pro Leu Glu Asn Thr Trp Pro Ala Pro Tyr Pro His Ser Lys Lys
145                 150                 155                 160

Leu Ala Glu Lys Ala Val Leu Ala Ala Asn Gly Trp Asn Leu Lys Asn
                165                 170                 175

Gly Gly Thr Leu Tyr Thr Cys Ala Leu Arg Pro Met Tyr Ile Tyr Gly
            180                 185                 190

Glu Gly Ser Arg Phe Leu Ser Ala Ser Ile Asn Glu Ala Leu Asn Asn
        195                 200                 205

Asn Gly Ile Leu Ser Ser Val Gly Lys Phe Ser Thr Val Asn Pro Val
    210                 215                 220

Tyr Val Gly Asn Val Ala Trp Ala His Ile Leu Ala Leu Arg Ala Leu
225                 230                 235                 240

Gln Asp Pro Lys Lys Ala Pro Ser Ile Arg Gly Gln Phe Tyr Tyr Ile
                245                 250                 255

Ser Asp Asp Thr Pro His Gln Ser Tyr Asp Asn Leu Asn Tyr Thr Leu
            260                 265                 270

Ser Lys Glu Phe Gly Leu Arg Leu Asp Ser Arg Trp Ser Phe Pro Leu
        275                 280                 285

Ser Leu Met Tyr Trp Ile Gly Phe Leu Leu Glu Ile Val Ser Phe Leu
    290                 295                 300

Leu Arg Pro Ile Tyr Thr Tyr Arg Pro Pro Phe Asn Arg His Ile Val
305                 310                 315                 320

Thr Leu Ser Asn Ser Val Phe Thr Phe Ser Tyr Lys Lys Ala Gln Arg
                325                 330                 335
```

```
Asp Leu Ala Tyr Lys Pro Leu Tyr Ser Trp Glu Glu Ala Lys Gln Lys
        340                 345                 350

Thr Val Glu
        355
```

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tgtaaaacga cggccagt                                                     18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
caggaaacag ctatgacc                                                     18

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
ggtaacggaa cccagggctc tccaggggca aat                                    33

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
ctcgagggcc atccaaagta gcagggat                                          28

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ggaacccagg gctctccagg ggcaaatga                                         29

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
cacagcctgg cacgttctag agagacaat                                         29

<210> SEQ ID NO 13
<211> LENGTH: 41
<212> TYPE: DNA
<213> ORGANISM: Artificial Sequence
<220> FEATURE:
<223> OTHER INFORMATION: Primer

<400> SEQUENCE: 13
tgtaaaacga cggccagtgg caaatgacca ttgaggtttc a        41

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
caggaaacag ctatgaccgt ggacgtactt ctcacctcat tt        42

<210> SEQ ID NO 15
<211> LENGTH: 40
<212> TYPE: DNA
<213> ORGANISM: Artificial Sequence
<220> FEATURE:
<223> OTHER INFORMATION: Primer

<400> SEQUENCE: 15
tgtaaaacga cggccagtgg aggagagagc aatgagtaca        40

<210> SEQ ID NO 16
<211> LENGTH: 51
<212> TYPE: DNA
<213> ORGANISM: Artificial Sequence
<220> FEATURE:
<223> OTHER INFORMATION: Primer

<400> SEQUENCE: 16
caggaaacag ctatgaccca tactatgcca ttttatacta tttaatattt a        51

<210> SEQ ID NO 17
<211> LENGTH: 45
<212> TYPE: DNA
<213> ORGANISM: Artificial Sequence
<220> FEATURE:
<223> OTHER INFORMATION: Primer

<400> SEQUENCE: 17
tgtaaaacga cggccagtga ttacttttct aaaatgagat gggag        45

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
caggaaacag ctatgaccgt tagcagtctt gaactctcct at        42

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
gtaccctgag tctgttacaa ccaccat                                              27

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
gtagaaatgg agctctagta gtcaaaacg                                            29

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
tgtaaaacga cggccagtgg tggggcacat agatctgtgt t                              41

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
caggaaacag ctatgaccga tatagtagaa ctgtcctcgg atg                            43

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
tgtaaaacga cggccagtgt taacccagtc tatgttggca at                             42

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
caggaaacag ctatgacccc tgagcttgtg cccttgtcac t                              41

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
caggacgtct cggtcgtcat ccacaccgcc t                                         31

<210> SEQ ID NO 26
<211> LENGTH: 31

```
<212> TYPE: DNA
<213> ORGANISM: Artificial Sequence
<220> FEATURE:
<223> OTHER INFORMATION: Primer

<400> SEQUENCE: 26
aggcggtgtg gatgacgacc gagacgtcct g                                    31

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
cactcacaga gagtttatca tgaatgtca                                       29

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
tgacattcat gataaactct ctgtgagtg                                       29

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
tgagggccct gcagaacccc aagaaggccc                                      30

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
gggccttctt ggggttctgc agggccctca                                      30

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
gattccagat ggagccttcc tttatccctg a                                    31

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
```

-continued

```
tcagggataa aggaaggctc catctggaat c                              31

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
ccggcacaag gagaccctga agtccaag                                  28

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
cttggacttc agggtctcct tgtgccgg                                  28
```